US011715024B1

United States Patent
McEntire et al.

(10) Patent No.: US 11,715,024 B1
(45) Date of Patent: Aug. 1, 2023

(54) ESTIMATING SOIL CHEMISTRY AT DIFFERENT CROP FIELD LOCATIONS

(71) Applicant: ARVA INTELLIGENCE CORP., Salt Lake City, UT (US)

(72) Inventors: John A. McEntire, Park City, UT (US); Thomas A. Dye, Austin, TX (US)

(73) Assignee: ARVA INTELLIGENCE CORP., Salt Lake City, UT (US)

( * ) Notice: Subject to any disclaimer, the term of this patent is extended or adjusted under 35 U.S.C. 154(b) by 227 days.

(21) Appl. No.: 17/171,887

(22) Filed: Feb. 9, 2021

Related U.S. Application Data

(63) Continuation-in-part of application No. 17/160,286, filed on Jan. 27, 2021.
(Continued)

(51) Int. Cl.
  *G06F 11/30* (2006.01)
  *G06N 5/04* (2023.01)
  (Continued)

(52) U.S. Cl.
  CPC ............... *G06N 5/04* (2013.01); *G01N 27/04* (2013.01); *G01N 33/24* (2013.01); *G06F 16/29* (2019.01);
  (Continued)

(58) Field of Classification Search
  CPC ........................................................ G06N 5/04
  See application file for complete search history.

(56) References Cited

U.S. PATENT DOCUMENTS

| 7,058,197 B1 | 6/2006 | McGuire et al. |
| 10,076,120 B2 | 9/2018 | Maltzahn et al. |

(Continued)

FOREIGN PATENT DOCUMENTS

| AU | 2017377078 A1 | 7/2020 |
| CA | 2439575 C | 9/2002 |
| CN | 109374860 A | 2/2019 |

OTHER PUBLICATIONS

"An Overview of Cubist", Rulequest Research, https://www.rulequest.com/cubist-unix.html, retrieved Jun. 1, 2021, 19 pages.
(Continued)

*Primary Examiner* — Phuong Huynh
(74) *Attorney, Agent, or Firm* — Kerr IP Group, LLC

(57) ABSTRACT

A system and method for interpolating soil chemistry variables to different plots of land is described. A first interpolation training model includes a machine learning model that receives soil composition information. A distance field training model generates spatial predictors that are applied to the machine learning model. The first interpolation training model prioritizes spatial smoothing over accuracy. A second interpolation training model is also applied that includes a distance weighting training model that more greatly weighs interpolated soil composition information closer to a point of interpolation than interpolated soil composition information that is further away to the point of interpolation. The second interpolation training model prioritizes accuracy over spatial smoothing. The illustrative crop prediction engine estimates soil chemistry values at different locations with the first interpolation training model and the second interpolation training model.

20 Claims, 9 Drawing Sheets

Related U.S. Application Data

(60) Provisional application No. 63/100,545, filed on Mar. 17, 2020, provisional application No. 62/995,948, filed on Feb. 20, 2020.

(51) Int. Cl.
  *G01N 33/24* (2006.01)
  *G01N 27/04* (2006.01)
  *G06N 20/20* (2019.01)
  *G06F 16/29* (2019.01)
  *G06N 5/01* (2023.01)

(52) U.S. Cl.
  CPC ....... *G06N 20/20* (2019.01); *G01N 2033/245* (2013.01); *G06N 5/01* (2023.01)

(56) References Cited

U.S. PATENT DOCUMENTS

| | | | |
|---|---|---|---|
| 10,136,646 | B2 | 11/2018 | Maltzahn et al. |
| 10,317,260 | B2 | 6/2019 | Duke et al. |
| 2005/0246066 | A1 | 11/2005 | Carney et al. |
| 2007/0240242 | A1* | 10/2007 | Modiano ............... G06Q 50/02 435/40.5 |
| 2016/0247082 | A1 | 8/2016 | Stehling et al. |
| 2017/0046639 | A1 | 2/2017 | Osborne et al. |
| 2018/0153174 | A1 | 6/2018 | Riley et al. |
| 2018/0249716 | A1 | 9/2018 | Riley |
| 2018/0251776 | A1 | 9/2018 | Riley |
| 2018/0260446 | A1 | 9/2018 | Shoham |
| 2018/0330247 | A1 | 11/2018 | Cohen |
| 2018/0330435 | A1* | 11/2018 | Garg ................. G06Q 30/0283 |
| 2019/0050948 | A1* | 2/2019 | Perry ................. G06V 20/188 |
| 2019/0057461 | A1 | 2/2019 | Ruff et al. |
| 2019/0059390 | A1 | 2/2019 | Djonovic et al. |
| 2019/0085352 | A1 | 3/2019 | Goldman et al. |
| 2019/0124855 | A1 | 5/2019 | Rowan et al. |
| 2019/0138962 | A1 | 5/2019 | Ehlmann et al. |
| 2019/0139158 | A1 | 5/2019 | Reich et al. |
| 2019/0156255 | A1* | 5/2019 | Carroll ............... G06Q 10/0635 |
| 2019/0227046 | A1 | 7/2019 | Parameswaran et al. |
| 2019/0325467 | A1 | 10/2019 | Perry et al. |
| 2019/0325533 | A1 | 10/2019 | Perry et al. |
| 2019/0347836 | A1 | 11/2019 | Sangireddy et al. |

OTHER PUBLICATIONS

"Description of SSURGO Database", National Resources Conservation Service Soils website, USDA, https://www.nrcs.usda.gov/wps/portal/nrcs/detail/soils/survey/?cid=nrcs142p2_053627, retrieved Jun. 1, 2021, 2 pages.
"Introduction to Geographically Weighted Regression", Feb. 6, 2009, https://www.bristol.ac.uk/media-library/sites/cmpo/migrated/documents/gwr.pdf, 9 pages.
"Modified Shepard's Method", Observable, Aug. 27, 2019, https://observablehq.com/@fil/modified-shepards-method, 4 pages.
"Selecting the Number of Clusters with Silhouette Analysis on KMeans Clustering", scikit-learn developers, https://scikit-learn.org/stable/auto_examples/cluster/plot_kmeans_silhouette_analysis.html, retrieved Jun. 2, 2021, 5 pages.
"The National Map", National Geospatial Program, USGS, https://www.usgs.gov/core-science-systems/national-geospatial-program/national-map, retrieved Jun. 1, 2021, 3 pages.
"UMAP: Uniform Manifold Approximation and Projection for Dimension Reduction", UMAP, 2018, https://umap-learn.readthedocs.io/en/latest/, 5 pages.
"Understanding the MUSYM Field on SSURGO Dataset?", Geographic Information Systems website, https://gis.stackexchange.com/questions/289590/understanding-the-musym-field-on-ssurgo-dataset, retrieved Jun. 1, 2021, 2 pages.
"What Does the Term UTM Mean? Is UTM Better or More Accurate Thank Latitude/Longitude?", USGS, https://www.usgs.gov/faqs/what-does-term-utm-mean-utm-better-or-more-accurate-latitudelongitude?qt-news_science_products=0#qt-news_science_products, retrieved Jun. 1, 2021, 5 pages.
Basu et al., Iterative Random Forests to Discover Predictive and Stable High-Order Interactions, PNAS, Feb. 20, 2018, pp. 1943-1948, vol. 14, No. 8.
Behrens et al., Spatial Modelling with Euclidean Distance Fields and Machine Learning:, European Journal of Soil Science, Sep. 2018, pp. 757-770, vol. 69, British Society of Soil Science.
Breiman et al., "Chapter 11: Classification Algorithms and Regression Trees", pp. 246-280.
Breiman, Random Forests, Machine Learning, 2001, pp. 5-32, vol. 45, Kluwer Academic Publishers, Netherlands.
Brownlee, "A Gentle Introduction to k-Fold Cross-Validation", Machine Learning Mastery, May 23, 2018, 70 pages.
Choi et al., "Multivariate Generalized Multifactor Dimensionality Reduction to Detect Gene-Gene Interactions", BMC Systems Biology, 2013, S15, vol. 7 (Suppl 6), pp. 1-11.
Einicke et al., "Iterative Smoother-Based Variance Estimation", IEEE Signal Processing Letters, May 2012, vol. 19, No. 5., pp. 275-278.
Expert.AI "What Is Machine Learning? A Definition.", web page, Mar. 2017, https://www.expert.ai/blog/machine-learning-definition/, accessed Jun. 1, 2021, 8 pages.
Fridgen et al., "Management Zone Analyst (MZA): Software for Subfield Management Zone Delineation", Agronomy Journal, Jan.-Feb. 2004, pp. 100-108, vol. 96.
Friedman et al., "Predictive Learning Via Rule Ensembles", The Annals of Applied Statistics, 2008, 41 pages, vol. 2, No. 3, Institute of Mathematical Statistics.
Janrao, "Management Zone Delineation in Precision Agriculture Using Data Mining: A Review", IEEE Sponsored 2nd International Conference on Innovations in Information Embedded and Communication Systems ICIIECS'15, Sep. 29, 2016, 8 pages.
Lin et al., "Combining GeoEye-1 Satellite Remote Sensing, UAV Aerial Imaging, and Geophysical Surveys in Anomaly Detection Applied to Archaeology", IEEE Journal of Selected Topics in Applied Earth Observations and Remote Sensing, Dec. 2011, pp. 870-876, vol. 4, issue 4, IEEE.
McInnes et al., "How HDBSCAN Works", 2016, https://hdbscan.readthedocs.io/en/latest/how_hdbscan_works.html, retrieved Jun. 2, 2021, 16 pages.
Meinshausen, "Node Harvest", The Annals of Applied Statistics, 2010, pp. 2049-2072, vol. 4, No. 4, Institute of Mathematical Statistics.
Moulavi et al., "Density-Based Clustering Validation", Proceedings of the 14th SIAM International Conference on Data Mining (SDM), Philadelphia, PA, 2014, 9 pages.
Ruczinski et al., "Sequence Analysis Using Logic Regression", Genetic Epidemiology, 2001, pp. S626-S631, vol. 21 (Suppl 1), Wiley Periodicals, LLC.
Science Direct, "Gaussian Model", Journal of Environmental Radioactivity, https://www.sciencedirect.com/topics/engineering/gaussian-model, retrieved Jul. 9, 2021, 13 pages.
Shah et al., "Random Intersection Trees", Journal of Machine Learning Research, 2014, pp. 629-654, vol. 15, JMLR, Inc. & Microtome Publishing.
Shah et al., Aging Investigation of Digital Circuit Using In-Situ Monitor, 2018 International Integrated Reliability Workshop (IIRW), 2018, pp. 1-4, IEEE.
TPI (Topographic Position Index), QGIS User Guide, https://docs.qgis.org/2.8/en/docs/user_manual/processing_algs/gdalogr/gdal_analysis/tpitopographicpositionindex.html; retrieved Jun. 1, 2021, 3 pages.
Yaghoubi et al., "Reduced Order Surrogate Modeling Technique for Linear Dynamic Systems", Mechanical Systems and Signal Processing, Oct. 2018, pp. 172-193, vol. 111, Elsevier.

* cited by examiner

Figure 1 - Prior Art

ESTIMATING SOIL CHEMISTRY AT DIFFERENT CROP FIELD LOCATIONS

CROSS REFERENCE

This patent application is a Continuation-In-Part of patent application Ser. No. 17/160,286 that was filed on Jan. 27, 2021 and entitled PREDICTING CROP YIELD WITH A CROP PREDICTION ENGINE, which claims the benefit of provisional patent application 62/995,674 filed on Feb. 7, 2020 and entitled METHOD AND APPARATUS FOR ESTIMATING SOIL CHEMISTRY AT ANY CROP-FIELD LOCATION;

this patent application claims the benefit of provisional patent application 62/995,948 that was filed on Feb. 20, 2020 and entitled METHOD AND APPARATUS FOR CLUSTERING GROUND TYPES FROM INTERPOLATED AND ENVIRONMENTAL COVARIATES; and this patent application claims the benefit of provisional patent application 63/100,545 filed on Mar. 17, 2020 and entitled METHOD AND APPARATUS FOR DETERMINING CROP-YIELD DRIVERS USING MULTI-DIMENSIONAL RESPONSE SURFACES; all of the applications are incorporated by reference in this patent application.

FIELD

The present disclosure relates to a system and method for estimating soil chemistry at different crop field locations. More specifically, the system and method blend and optimize a first interpolation training model that prioritizes spatial smoothing over accuracy and a second interpolation training model that prioritizes accuracy over spatial smoothing.

BACKGROUND

Geographic, weather, agronomic and environmental factors affect crop production. The factors that control crop production vary. Growers have various options including, but not limited to, changing planting strategies and controlling soil composition. However, depending on various conditions that may be out of the growers' control, growers may not be able to change planting strategies and control soil composition. For example, changing weather conditions are outside of the growers' control.

Additionally, the quantity of information and possible applications of seed and fertilizer are so vast that growers can easily be overwhelmed by choices and options presented by local agronomists and farm consultants. Typically, the growers' decision making process results in reduced crop production due to an incomplete set of information. Also, too much information, or lack of precision in the information that conflicts with a clear cut decision affects crop production.

Despite the increasing amounts of data in agriculture, the adoption rates of seeds from major seed companies, the application of synthetic fertilizer, and various chemical innovations, the worldwide crop yield growth rates have plateaued to less than 1% annually. In order to meet the United Nations anticipated food demand in 2050, crop yields must grow at 1.8% per year from a 2014 baseline.

The production plateau of less than 1% is occurring at the same time as farmers are receiving more information from remote sensing technologies like unmanned aerial vehicles (UAVs) and in situ monitors along with geospatial monitoring of fertilizer and harvest yield data. This information has not produced major improvements in total factor productivity.

Generally, the application of soil nutrients to improve crop yield has been based on the results of manual soil sampling and on-off laboratory analysis. Recent advances in farm equipment have improved the ability to apply chemicals and nutrients with higher precision using farm equipment that allows variable rates of nutrient or seed-type selection at the sub-acer application precision across entire plots of land at large scale.

However, little has been done to increase the understanding of the detailed soil and environmental characteristics at higher spatial resolutions to set the parameters of farm equipment for high precision seed and nutrient applications.

Thus, it would be beneficial to understand the soil chemistry and environmental characteristics at higher spatial resolutions while correcting for data inaccuracies and a limited number of data samples.

SUMMARY

A system and method for interpolating soil chemistry variables at a plurality of plots of land is described. The system includes a geospatial database associated with a crop prediction engine. The geospatial database receives soil composition information for each of the plots of land, in which the soil composition information includes at least one of measured soil sample results, environmental results, and soil conductivity results.

The crop prediction engine applies a first interpolation training model that includes a machine learning model that receives the soil composition information. Additionally, a distance field training model generates spatial predictors that are applied to the machine learning model. The first interpolation training model prioritizes spatial smoothing over accuracy. Spatial smoothing removes inaccurate interpolated results and accuracy relates to the degree the interpolated results conform to a correct value. In the illustrative embodiment, the first interpolation training model includes a random forest prediction model.

Also, the crop prediction engine applies a second interpolation training model that includes a distance weighting training model that more greatly weighs interpolated soil composition information closer to a point of interpolation than interpolated soil composition information that is further away from the point of interpolation. The second interpolation training model prioritizes accuracy over spatial smoothing. In the illustrative embodiment, the distance weighting training model includes inverse distance weighting (IDW).

Additionally, the crop prediction engine estimates a plurality of soil chemistry values at a plurality of different locations with the first interpolation training model and the second interpolation training model.

In the illustrative embodiment, the crop prediction engine generates non-optimized interpolated soil chemistry values by blending the first interpolation training model and the second interpolation training model with a blending term that separately weighs the first interpolation training model and the second interpolation training model.

Furthermore, the crop prediction engine optimizes the blending of the first interpolation training model and the second interpolation training model by performing one or more error calculations. More specifically, the crop prediction engine optimizes the blending of the first interpolation training model and the second interpolation training model by applying a hyper parameter tuning loop to the first interpolation training model and the second interpolation training model. The hyper parameter tuning loop optimizes blending the first interpolation training model and the second interpolation training model by performing one or more error calculations.

FIGURES

The present systems and methods will be more fully understood by reference to the following drawings which are presented for illustrative, not limiting, purposes.

DESCRIPTION

Figure 1:
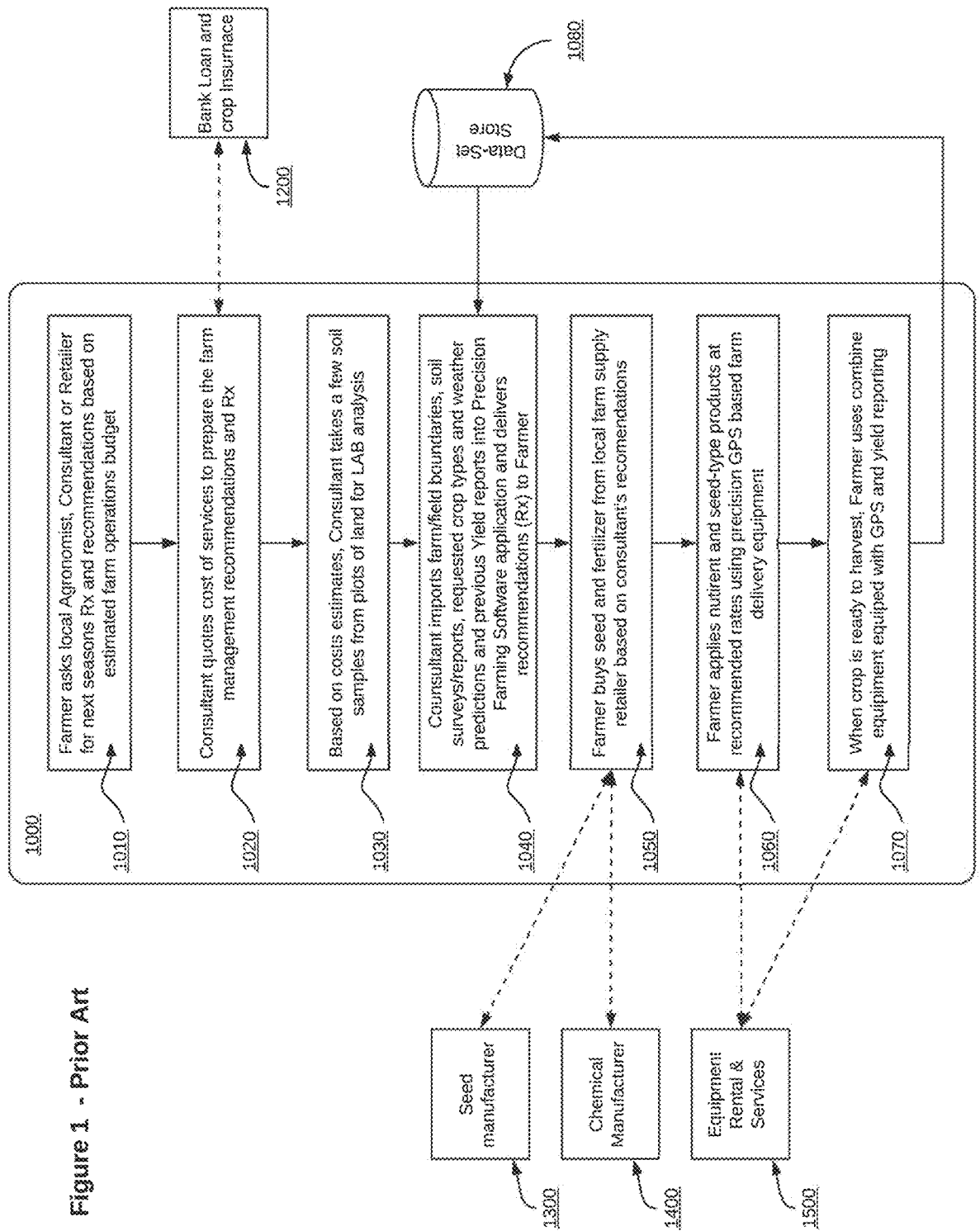
FIG. 1 shows a management flowchart for farmers running a typical precision farming operation.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and methods described herein may vary as to configuration and as to details. The following detailed description of the illustrative embodiments includes reference to the accompanying drawings, which form a part of this application. The drawings show, by way of illustration, specific embodiments in which the invention may be practiced. It is to be understood that other embodiments may be utilized, and structural changes may be made without departing from the scope of the claims. It is further understood that the steps described with respect to the disclosed process(es) may be performed in any order and are not limited to the order presented herein.

A system and method for interpolating soil chemistry variables to a plurality of locations within a plot of land is described. The system and method include a trained machine learning training model with at least one set of measured soil chemistry variables, soil conductivity and possible environmental characteristics that are used as inputs to accurately predict soil composition estimations at arbitrary locations within each of a plurality of plots of land. The illustrative embodiment uses machine learning methods in combination with distance weighting models to predict soil chemistry characteristics at any arbitrary location within one or more plots of land. The introduction of a hyper parameter tuning loop optimizes the coefficients used in the model to optimize the estimated soil characteristic predictions.

The system and method use Machine Learning (ML) to estimate higher resolution soil chemical characteristics for any location to produce an interpolated, higher resolution grid of soil chemistry estimates that can be used in any high precision agriculture practice. Thus, the system and method show a precision agriculture soil management practice using the system and method for building a generic model to accurately predict soil chemistry at any arbitrary location in different plots of land.

The systems and methods described herein use explainable artificial intelligence (AI) and machine learning (ML) in a cloud computing environment to enable a crop prediction engine. Additionally, the systems and methods import various data sets from disparate sources and apply AI and/or ML to the data sets for different farmland acreage. The systems and methods described herein are used to optimize agricultural production by improving crop yields and/or modeling crop yields for different seed types, using different nutrients in different locations.

Generally, geographic, weather, agronomic and environmental factors affect crop production. The factors that control crop production vary. Growers have various options to change planting strategies and control soil composition, however, there are many variables that growers are unable to control.

The systems and methods presented herein improve crop production. Additionally, the systems and methods presented herein may be used to determine carbon and $CO_2$ extraction and interaction between plant and respective spatially related soil zones. Furthermore, the systems and methods described herein apply at least one data set of soil chemistry, spatial boundaries, previous planted crop-type, cover crops and previously recorded crop-yield data sets as independent input variables used to train a crop prediction engine using machine learning.

Further still, the systems and methods described herein provide at least one learned model for the purpose of soil classification and soil fertility zonation, which is hereafter called "crop response zones," "clusters," or "ground types." The terms "crop response zones," "clusters," or "ground types" may be used interchangeably. The classification of crop response zones are crop specific and may allow crop planning and analysis through the precise placement of nutrient applications and specific seed-type selections. The machine learning used by the crop prediction engine predicts crop responsiveness for seed types planted in different ground type zones.

Thus, the systems and methods presented herein provide a more precise agriculture soil management and recommendation of seed-types to accurately predict crop responsiveness to differing soil characteristics with different seed-types planted in one or more plots of land.

Further yet, the systems and methods presented herein describe a new class of machine learning (ML) computing platform and software tools to aid farmers and their suppliers in predicting crop yield, managing risks, achieving sustainability objectives, and optimizing input costs. The illustrative systems and methods focus on the creation and use of ML to increase total factor productivity for commodity and biofuel crops while also improving water, nitrogen, and phosphorus use efficiency.

Additionally, the illustrative systems and methods leverage massively multi-scale, multi-modal data to gain insight into the driving forces behind ecosystem services. Current methods of remote sensing measure multiple aspects of cropping systems but fall short in providing meaningful, actionable intelligence for enhancing a farm or field's agronomic health. Using geospatial technology, soil chemistry analysis, environmental DNA (eDNA) sequencing, and related technologies to discover and define soil regimes, the ML tools of the described systems and methods enable farmers to tailor crop inputs, accounting, and farm management operations for a high degree of soil heterogeneity; and this is a critical missing link, since above ground signatures (e.g., plant growth/activities) are known to be closely linked to below ground properties (e.g., soil moisture/texture/salinity, nutrient, microbial activities).

More specifically, there have been recent studies using UAV reconnaissance and geophysics which have quantified co-variability between above ground signatures and below ground signatures. These studies further identified key controls and limiting factors in ecosystem functioning. In particular, simultaneously using UAV data and geophysical data have identified the soil-plant co-variability and the limiting factors for a soybean yield.

In general, the systems and methods provide a crop prediction engine that can be trained with ML to predict a crop yield in a particular location. Referring to FIG. 1 there is shown a management flowchart for farmers running a typical precision farming operation. The FIG. 1 flowchart shows the typical process used by farmers to grow crops on plots of land under their management. Most of the prior methods use manual communications between partners and non-computer-automated procedures to accomplish crop production and farm management.

Block 1000 presents an illustrative method that shows the typical interactions performed by farmers during a typical growing season. Suppliers may include seed suppliers and manufacturers 1300. Additionally, suppliers may include chemical and nutrient suppliers and manufacturers 1400 and equipment suppliers that may provide farm equipment for purchase, rental, or services for supplies and to apply various products to the fields.

Additionally, the prior precision farming applications typically require some form of client device for storage 1080, which stores data sets used by the farmer or farmer consultants to improve farm management efficiency with additional precision. Data collection is necessary for farm management analysis, which typically includes yield analysis. Farm management analysis is used to determine what kinds of crops to grow, seed selections to be used and the nutrients required to meet desired crop production output. Furthermore, farmers may interface with banks and crop insurance companies 1200 for the finances and risk mitigation through crop-insurance as necessary for farm management operations.

FIG. 1 presents an illustrative method 1000 that a farmer may apply for seasonal activities during the management of at least one farm using precision farming techniques. The illustrative method 1000 is initiated at block 1010 where the farmer obtains recommendations from an agronomist that may be considered as the "specialist" or "consultant." By way of example and not of limitation, the recommendations may include application prescriptions in preparation for field treatment and planting information prior, during and post planting seasons. In addition to prescriptions and recommendations, the agronomist may also play a part in advising budget and financial information needed by the farmer to meet management and financial goals.

At block 1020, the consultant quotes the cost of services which may include seed-type, nutrient applications, and application rates across the farm by field or sub-field area.

The method then proceeds to block 1030 where the agronomist or consultant may need to sample the soil in various areas of the farm or by field to get more precise information about particular soil characteristics prior to seasonal planting. Soil samples may be gathered with a spatially sparse resolution due to the high cost of lab analysis and sampling procedures. In other instances, agronomists may resort to third party databases such as Soil Survey Geographic (SSURGO) database or Natural Resources Conservation Service (NRCS) soil maps available from the United States Department of Agriculture (USDA) that contain historical soil chemistry and soil texture data to calculate recommendations.

At block 1040, agronomists and crop consultants may import and manually process additional data to assist them with application prescriptions and recommendations. Some additional information may include actual farm boundaries, field boundaries, cover crop activities, previous seasonal harvest information along with short and long term weather forecasts. While most of the farmers, agronomists and consultants use university or third party formulas to look up recommendations—some will apply blanket applications that do not take in to account the precision recommendations provided by well-known agricultural software applications.

After the farmer makes the farm management and planting decisions based on the decisions made at blocks 1010, 1020, 1030 and 1040, the farmer proceeds to block 1050 where the farmer buys seeds and fertilizer from a local farm supply retailer based on the consultant's recommendation. More specifically, the purchases of recommended seed-types and chemical nutrients are made from illustrative seed manufacturers 1300, chemical manufacturers 1400 and other such suppliers. In some instances, farmers may select these supplies from a local retailer or have the supplies delivered to the farms or application locations. In other instances, the farmer may hire third party services or rent equipment for seed-planting or nutrient applications at the consultant's or agronomist's recommended quantities and application rates.

At block 1060, the farmer applies nutrient and seed type products at recommended rates using precision GPS based farm delivery equipment. For precision farming, sub-field application precision is typically accomplished by farm equipment or farm implements that employ the Global Positioning System (GPS) allowing for 1 to 5 Hz application cycles from precision based equipment based on application delivery rates and speeds.

At block 1070, the crop is ready to harvest and the farmer uses combine equipment equipped with GPS and yield reporting. As the growing season comes to an end, the farmer prepares for the harvest. The farmer may have secured harvesting equipment by purchase through bank loans 1200, personal funds or through equipment rental 1500 to complete the harvesting of production crops. For harvesting, most modern combine equipment is also equipped with GPS and crop-yield monitoring sensor capability. The yield information obtained by the combine is a critical component of precision agriculture practice because previous seasonal yield results are critical to understanding profit and loss.

This yield information can also be used by the crop prediction engine systems and methods described in further detail below; more specifically, the yield information can be used to train the crop prediction engine. Precision application and harvesting equipment are often equipped with data collection apparatus as described in the illustrative embodiments presented below. Also, data collection information may be used by both the crop prediction engine described below and the previous well-known solutions.

Figure 2:
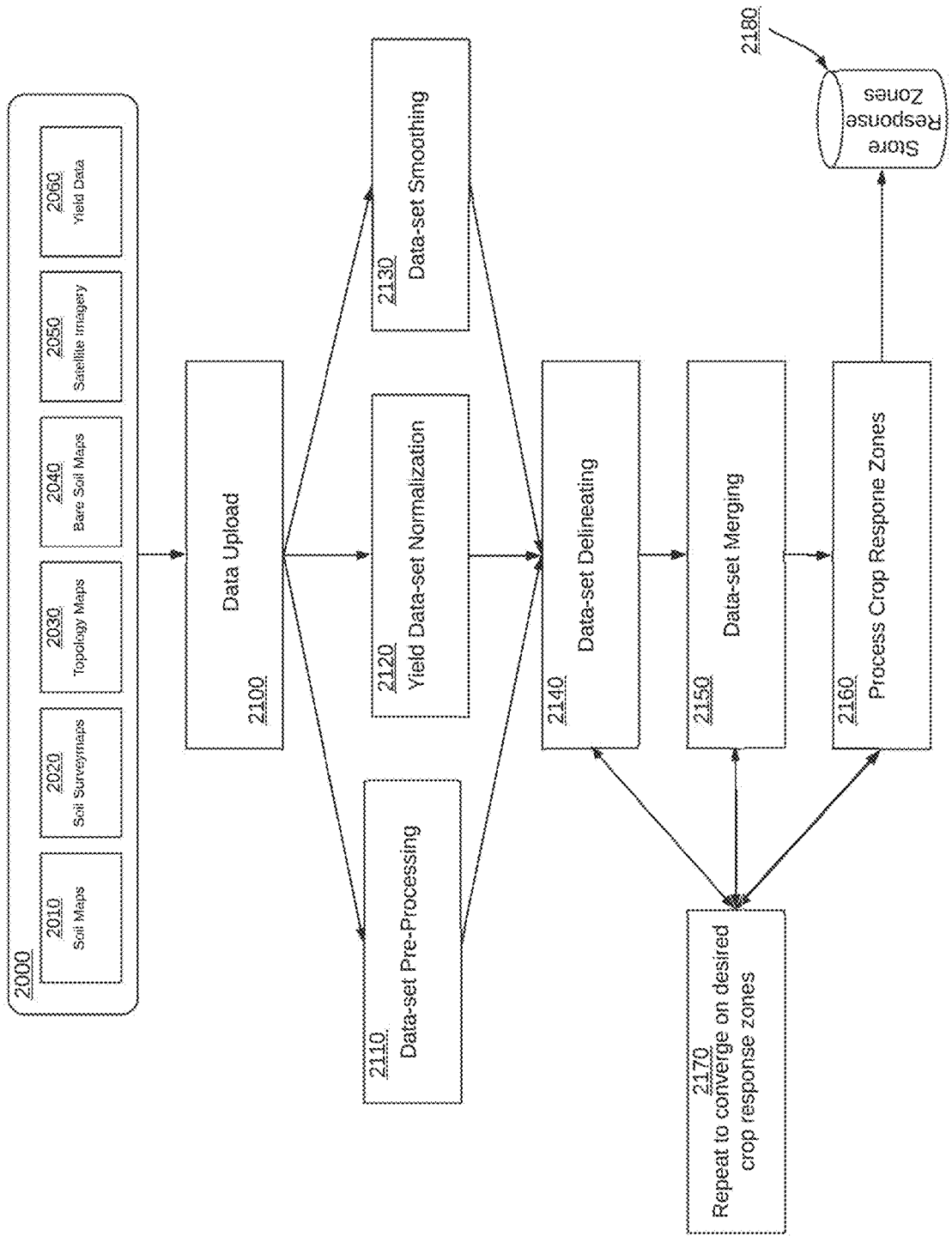
FIG. 2 shows an illustrative flowchart for a crop modeling software application used by growers to estimate farm management operations and predictive yield.

Referring to FIG. 2, there is shown an illustrative flowchart for a crop modeling software application used by growers to estimate farm management operations and predictive yield. At process block 2000, a variety of different data sets are shown. In general, data set ingestion and processing of the different ingested data sets occurs at process block 2000. Process block 2000 also indicates the transient and permanent data set types that may be input for processing. Data sets may be obtained from one or more of the farmer's partners, associations, agriculture organizations, third party satellite companies, government agencies and the like.

Transient feature data for crop-yield 2060 represents land or field characteristics that vary from time to time. In the context of agricultural crop response zones, examples of transient feature data may include yield and/or soil characteristic data. Yields for example may vary within a field from one harvesting season to another. Yield data 2060 may include historical yield maps that represent spatial and temporal yield patterns for the sub-fields. Yield data 2060 may include information about yields of crops harvested from an agricultural field within one year or within several years. Yield data may also include additional geometry information such as a field boundary, a field size, and a location of each sub-field within the field. Yield data may be provided from different sources. Examples of the sources for yield data may include research partners, agricultural agencies, agricultural organizations, growers, governmental agencies, and other such sources.

Also, transient feature data for soil maps 2010 represents land or field characteristics that vary from time to time. Based on weather patterns, erosion, soil carbon emissions, crop-types, nutrient applications and other environmental conditions, soil chemistry can also be considered a transient feature. Soil characteristics for example may also vary within a field or sub-field and from one season to another. Soil characteristics may also include historical data maps representing spatial and temporal patterns but also may not vary as much as other environmental or crop yield transient conditions. Examples of the sources for soil characteristics may include governmental agencies, institutions, agricultural organizations, universities and sensor data from growers or sensor data directly from laboratory analysis of soil samples.

Data for soil characteristics 2010 of a field may be obtained based on soil samples collected from sensors in one or more plots of land or fields. In one illustrative embodiment, soil sampling may be performed using various sampling techniques. For example, for precision agriculture collecting soil samples may be performed at an approximate resolution of one sample per two acres or may vary with samples taken at higher or lower spatial resolutions. Lower resolution samples may be taken at one sample per 10 acres or at one sample per field leading to lower precision data sets for modeling. The samples may be collected at grid points within a field and the grid may roughly form a rectangle or may have no fixed geometry constraints. The original sample measurement data is typically gathered from samples analyzed by local or national laboratories and results are reported in the form of a textural report of the soil chemistry attributes surrounding the sample location. Soil data sets of this form may be stored in files on computer servers or may only be available in paper form.

When soil samples are provided from different sources, i.e. different laboratories, there might be some differences in soil sampling methods, terminology and units. The differences may be caused by nomenclature or different accuracy measures with which the samples were collected. In some instances, differences of chemical characteristics may be a result of different sampling depths at which the soil was sampled. To minimize the impact of such differences, the data sets may be preprocessed by one or more computing devices or manually manipulated to normalize the samples in some data sets. Thus, preprocessing of soil data sets may include removing duplicated samples, samples with no associated values, samples with no geographical coordinate information, and samples with incorrect coordinates and geographical information.

Although some satellite data sets may be considered as a permanent data set feature, some satellite characteristics for an agricultural field may also be considered transient. Satellite feature-sets are typically determined based on temporal satellite maps. Satellite image data may be provided at different spatial, spectral, and temporal resolutions. The satellite maps may provide information about agricultural crop assessment, crop health, change detection, environmental analysis, irrigated landscape mapping, yield determination, and soils analysis. The images may be acquired at different times of the year and multiple times within a year.

Transient satellite data, aircraft fly-over and drone-collected data sets are typically also used for crop growth, pest control and nitrogen content analysis. Many of the previous learning platforms are dependent solely on normalized difference vegetation index (NDVI) readings to determine prior season crop production and yields used as input covariates for ML model training. Such transient data sets are important for bulk understanding of trends but often times do not yield the necessary results for high precision yield prediction modeling.

Generally, the term "covariate" refers to a dependent input variable data-set or data-sets that are used as input data to train or tune a Machine Learning (ML) training model. Sometimes, the term "covariate" may be used to refer to an "independent variable" that may also be used to train or tune one or more ML training models.

Permanent feature data 2020, 2030, 2040, are more commonly used and represent characteristics that remain relatively unchanged from one season to another. In the context of agricultural crop response zones, examples of permanent feature data for a field may include characteristics of soil texture, topology and terrain of the farm or field. This permanent feature data is considered permanent because such data usually does not change from one harvesting season to another. Permanent feature data may be obtained from soil survey maps, satellite maps, and bare-soil maps. Permanent feature sets may be provided as data sets from satellite imaging 2050 such as RapidEye, SSURGO soil image data sets, farm/field polygonal boundary data sets and National Elevation Dataset (NED) or USGS elevation map data sets.

Soil survey characteristics may also be provided in the form of soil survey maps as shown in process block 2020. One source of the soil survey maps that contains soil survey data of most areas in the United States is the SSURGO database. Soil survey maps from SSURGO may also be considered a permanent data set. Although soil survey maps may represent a qualitative assessment and lab-analyzed sample data, soil survey maps are considered permanent because most soil survey maps available from government agencies are historical in nature representing overall soil characteristics. The SSURGO survey maps, for example, provide a low resolution of soil measurement data and may be used in the absence of high resolution soil sample data. Although the soil chemistry and texture data available in the SSURGO survey maps may be sufficient for the purpose of supplemental data, they are not sufficient standing alone for crop response zone creation. In a particular implementation, the applicable soil texture data is at mukey (a map unit key) level 2, which means that the value of soil texture properties is uniform over the entire spatial polygon and may serve as a substitute for other soil characteristic data set sources.

A typical soil survey dataset from SSURGO is organized as a set of individual map units, each of which covers a polygon area. The data associated with each polygon may include soil chemistry properties and soil texture data, and the data may be provided at different spatial resolutions. The data may or may not be associated with specific geographical point locations.

Historically, the SSURGO data for a set of fields of interest is provided as a set of spatial polygons. The set of polygons may be processed by determining whether the soil texture data was missing for an entire polygon, and if so, a k-Nearest Neighbor (kNN) set of data points may be used to interpolate one or more missing data points. Furthermore, the sand, silt and clay percentages may be normalized to add up to 100%. Since third party soil databases like the SSURGO maps from the USDA do not provide a high resolution of soil measurement data, the soil texture data available in the SSURGO maps may be insufficient for the purpose of high-precision field-zone creation.

Topology characteristics 2030 of a field may include geographical and elevation characteristics of the field. Topology characteristics may include elevation data for an agricultural field, and other topographical properties that may be derived from the elevation data such as the wetness index by calculated slope information as a component of the digital elevation modeling. The wetness index may also be referred to as a Composite Topographic Index CTI, a Topographic Position Index (TPI) indicator, an aspect, a flow direction, and a slope. Digital elevation data sets may also be obtained from different sources, including the National Elevation Dataset (NED). The NED usually provides a resolution of about a third of an arc-second.

Satellite images at this resolution may depict variations in organic matter and drainage patterns. Soils higher in organic matter can be differentiated from lighter, sandier soil that has a lower organic matter content. This information may be used in conjunction with other types of maps to define management zones for a field.

Other examples of satellite imagery 2050 include bare-soil maps. Bare-soil map data sets 2040 may include bare-soil characteristics determined based on bare-soil satellite imaging. Examples of such maps may include satellite images from RapidEye images. A typical RapidEye image for a farm or field may contain per-pixel percentage reflectance values for five different bands: red, red edge, blue, green, and near-infra-red (NIR). In some embodiments, each pixel represents 25 square meters, or a 5 meter by 5 meter area. Using the RapidEye images may provide soil characteristics that may not be available when other types of images are used. For example, the RapidEye data usually represents topsoil better and deeper than other types of images.

For example, a set of bare-soil maps 2040 may be pre-processed for each field or for large scale analysis over many fields. The images that contain cloud cover may contaminate image quality and may be discarded or use an ensemble of VIR and SAR satellite technology to compensate for cloud cover contamination.

In general, process block 2000 represents one or more of the raw input variables, features, feature-sets, data sets or covariates used to train the crop prediction engine. At process block 2100, input data sets may be uploaded to permanent storage through one of many client devices as illustrated in further detail below in FIG. 3A. Uploads from program instructions in process block 2100 may also be data imports from other data-sources retrieved in the form of Application Programmable Interface (API) software, or by other means known to one skilled in the art. Besides uploading data features from database systems or storage platforms, pulling data, importing data, or downloading data from those database systems or storage platforms may also be represented in process block 2100. Some client devices are used to upload data sets dedicated to only the uploading or data retrieval process.

The upload process may be part of the crop management software running at least partially in one or more client devices. The upload process may also be enabled through client devices with network connections directly from third parties such as equipment manufacturers, agriculture consultants and farm co-ops or retailers.

By way of example and not of limitation, the process of uploading data sets 2100 to the illustrative crop prediction engine 4000 (shown in FIG. 3A) may be performed by the various client devices 3010 through 3080 (shown in FIG. 3A) or the client devices 4400, 4500 and 4600 (shown in FIG. 4); the application computing cluster 4100 (shown in FIG. 3A); or any other such device capable of receiving or generating a data set 2000.

Referring back to FIG. 2, process block 2110, process block 2120 and process block 2130 represent program instructions for pre-processing, normalization processing and smoothing of imported data sets 2000 after importing through data upload 2100 program instructions. Program instructions for process blocks 2110, 2120 and 2130 may be executed selectively, optionally, sequentially, or in parallel. The manner in which the tasks are performed may vary based on the implementation and the quality of received data set data. For example, some of the received data from various data sets may need preprocessing, but not smoothing. Other data may need only normalization processing, while other data may be normalized naturally as it traverses a random forest (RF) machine learning model and, thus, does not need pre-processing or normalization. Selection of one or more of process blocks 2110, 2120 and 2130 may be based on a manual inspection or a machine based inspection of the received data and may be performed in process block 2000 prior to the data set upload by client application program instructions at process block 2100.

Data sets 2000 may include sub-field observations that further include contaminated observations. Contaminations may be caused for a variety of reasons, for example, the way the crops are harvested, or by the way the data in each data set is collected or recorded. The contaminated observations may include outliers, invalid data, redundant data, missing data, and the like. In one embodiment contaminated data may be imputed to resolve areas where training data is required to enable crop-yield predictions by the ML model.

Program instructions for pre-processing data sets, indicated in process block 2110 program instructions, may include identifying data items that are outliers, invalid, redundant, missing or collected data from outside a field boundary. Such data may be removed, substituted, or imputed from an average from nearest neighbor data, supplied from alternate data set sources or substituted by alternate data sets from previous seasonal results. For example, missing yield data from one season may be substituted or averaged from another season. Pre-processing may also include identifying and removing the data set observations collected from one or more plots of land on which multiple crops were planted in the same season. Pre-processing may involve data set removal when data is considered to be redundant across one or more fields.

Pre-processing of data set data may also be performed to reduce or eliminate invalid data, which is also referred to as removal of noise observations or "de-noising" of data within particular data set inputs. Noise reduction is the process of removing noise from a raster image, vector, polygonal or textural based data set and may be necessary for feature preservation. De-noising of data within data sets may be based on a manual inspection to identify when noise is present or through machine-based inspection of the received data. De-noising may also be performed in the program instructions of process block 2000 prior to data set uploading. Pre-processing may include identifying the noise observations, and replacing the noise observations with approximated values or by other means as known to one knowledgeable in the art.

Process block 2120 represents the program instructions for normalization and imputation of yield data between different crop-yield data sets received from different sources. Imported data sets may be analyzed to determine that sufficient crop-yield data are available for ML model training or that crop-yield data are sparse or missing for at least one field within one or more farms. If less than two years of crop-yield data for any field are provided, then the yield maps for years not provided may be supplemented and sourced by other means. Supplemental crop-yield information may include data sets from fly overs, drones or satellite images and may also include crop-yield data sets from organizations, government agencies, third party agronomist groups, agricultural co-op retailers or by other means. Additional data set information may be used to supplement farm or field areas where crop-yield data is sparse, noisy, or missing. The additional crop-yield data sets may be averaged, added, subtracted, or substituted with other data sets to provide multiple years of crop-yield data sets for crop-response modeling.

Additional preprocessing and filtering of the crop-yield data sets 2120 may include adjusting the data values to account for grain moisture. By adjusting for grain moisture crop-yield data records can be corrected for different seasonal values where the crop-yield data is different from averages assigned to certain crop-types. For example, the standard moisture level for corn is typically 15%. Additional processing may also include correcting yield productivity data to account for data inaccuracies when experimental crop-yield data is provided. This may include correcting the crop-yield data if the data was pre-smoothed by one or more of the crop-yield data providers. This type of additional processing is recommended to reduce the effect of improperly smoothed crop-yield data on the results of the crop response zone creation.

Pre-processing of data set input variables, performed by the program instructions of process block 2110 and the normalization of crop-yield data 2120, may also require transformation from one geo-spatial coordinate system type to another. This transformation to a common coordinate system allows the unification of imported data sets into a common format. For example, transformation from latitude-longitude coordinate system to the Universal Transverse Mercator (UTM) coordinates results in mapping all data set coordinates onto a grid that has been previously defined for one or more locations. Transformation from other coordinate standards to a single standardization format allows data set records to be mapped to one common format for multiple different locations and/or the same location when different imported data set records have different reference coordinate systems. As a further example of coordinate transformation, if the received data was sampled in the system other than the UTM, then pre-processing of data may include adjusting the received data sets to some known grid or area UTM resolution. This may also include programmatically projecting the received data set data onto the UTM coordinates. Missing sample values may be interpolated at the UTM coordinates from the available data using a Gaussian model with a constant trend and parameters that are obtained using a maximum likelihood estimator.

Additionally, the pre-processing of input data 2110 may integrate topological information from digital elevation maps, Compound Topographic Index (CTI) or from farm/field equipment that directly monitors field elevation during planting, harvest, and nutrient applications. The elevation map services may be used for multi-resolution visualizations to explore hillsides, aspect, slope, as well as contour maps in raster image formats. Included in some governmental agencies, like USGS, is the ability to download through an API point values for elevation based on GPS coordinates. The data sets originating from Digital Elevation Maps (DEM) may be used to calculate slope data and CTI wetness index. Pre-processing may also include conversion of DEM data sets into a normalized wetness index used as input covariates to train the crop prediction engine.

The ensemble of DEM data sets and digital elevation input from farm and/or field equipment may be normalized and used to determine elevation and slope information used to build a composite wetness index for the areas of interest.

In the illustrative embodiment an ensemble of covariates containing multiple elevation data sets may be used to build a Random Forest (RF) generalized DEM model. By way of example and not of limitation, Inverse Distance Weighting (IDW) or other forms of interpolation, as known to those in the art, may be used to average the multi-dimensional DEM covariates within the farm and/or field location boundaries. Additional steps may be needed to normalize, apply weighting and transformation to the separate inputs formatting covariates prior to the interpolation. The interpolated output of the results may be used to build a comprehensive wetness index model for one or more farms or fields.

In the illustrative embodiment a combination of the multiple DEM sources require transformation between various data units to form a common unit format. Additionally, transformations between raster, point and polygon formats may be needed to unify the separately sourced DEM input data sets to form an ensemble of unified DEM data. For example, processing data set transformations to UTM coordinate representation and further performing transformations between point and raster coordinates from both farm equipment based DEM data and database DEM registries may be required. Interpolated DEM results may need further conversions and normalizations in order to form the ensemble of elevation averages used for wetness index determinations to train one or more crop prediction models.

Additionally, further pre-processing of the ensemble of DEM interpolated variables may include extracting cell values of the elevation raster where crop-yield or soil characteristics projected within a spatial point lies. If no cell raster, point, or polygonal area is found for the DEM projection within the farm and/or field boundaries of interest, then an indication of no DEM values may be returned.

In projecting the image data onto the UTM coordinate system, values of the image data at the location points of the various data sets 2000 may be obtained by rasterizing the data sets. The results may be transferred to data set raster cells. If one cell of one or more data sets is covered by multiple imagery bands of data points, then an arithmetic mean of the values may be used to associate the data points with the raster cells. For example, pre-processing SSURGO soil data coming from governmental agencies or third parties for analysis would require a projection of the coordinates of the spatial polygons into UTM coordinates. Once such transformation is completed, the SSURGO polygons may be overlapped onto the spatial locations of the crop-yield training data collected for the particular plots of land being modeled.

Process block 2120 further represents the program instructions for yield data set normalization of the received yield training vector. In the illustrative embodiment, the crop prediction engine uses the RF module to complete the data normalization as a function of the nature of the random forest, and thus process block 2120 may not be needed. Crop-yield normalization may also be required across different crops, farms, and fields.

Historically, data density processing includes using an Empirical Cumulative Distribution Function (ECDF) transformation. The ECDF transformation may be performed on the crop-yield data sets for each field and year so that the transformed crop-yield data is within a certain range across different crops and fields. For example, the ECDF may be applied to the received yield data to transform the data into transformed yield data in a normalized range. Once the yield data is transformed, the transformed yield data may be compared across different years and across different crops, such as corn, soy, or wheat.

In the illustrative embodiment, a separate random forest module may be used for each different crop type to be planted—by using the random forest module there is no need for an ECDF transformation between crop types.

Process block 2130 represents program instructions for smoothing received data. Data smoothing may include testing whether any crop-yield data records are missing, whether the crop-yield data records need to be further smoothed, or whether certain crop-yield data records need to be removed or interpolated. Spatial smoothing is a process of removing inaccurate observations from the collected crop-yield observations and defragmenting the obtained delineated zones. Historically, the spatial smoothing may be performed using a kernel-smoother or a stationary Gaussian process.

Depending on the quality of the received raw data, data smoothing may be performed on either raw data or pre-processed data. A kernel smoother is a statistical technique for estimating a function of observations when no parametric model for the function is known. The resulting estimated function is usually smooth and may be used to remove the noise observations from a set of yield data. Kernel smoothers are reliable and useful nonparametric estimators and may be selected to perform the spatial smoothing of the yield data. Examples of kernel smoothers that can be used to smooth the yield data include Gaussian kernel, inverse distance weighting kernel, rectangular kernel, triangular kernel, bi-square kernel, tri-cube kernel, and tri-weight kernel.

Process blocks 2140-2170 represent the programing instructions required for clustering farm and/or field areas into crop response zones. Clustering is a process of grouping data, i.e. crop response zones, into clusters and determining cluster labels for the clusters. Clustering the zones 2150 may be performed by merging small zones with larger zones. For example, zones with sizes smaller than a particular size may be merged with their most similar large neighboring zones. The particular size may be set manually or by automatically using database lookup, programmatically or by use of fixed configuration data or as a combination of one or more clustering methods.

Process block 2140 represents the program instructions for pre-processed data representing transient and permanent characteristics of an agricultural field used to delineate a set of crop response zones for an agricultural field. Historically, the set of delineated crop response zones may be represented using stored digital zone boundary data. Zone characteristics may be created by applying one of many delineation methods including centroid-based approaches, such as the K-means approach, or a fuzzy C-means approach.

The process executed in process block 2140 may be repeated by program instructions of process block arrow 2170 one or more times until the quality of the created response zones is satisfactory. The process may be repeated using different criteria, different parameters, or different parameter values.

A set of delineated crop response zones may be analyzed to determine whether some of the zones may be merged as represented by the program instructions in process block 2150. For example, a set of delineated management zones may be analyzed to identify small zones and to determine whether the small zones may be merged with neighboring larger zones. Small zones may be identified automatically by a computer system, or manually by a user of the computer system. The computer system may display information about the set of first response zones to a crop grower in a graphical user interface that is programmed with widgets or controls to allow the grower to remove undesirable fragmented small zones, or to merge the fragmented small zones with larger zones at process block 2150. The merging of zones results in obtaining a set of merged response zones. There may be components of clusters that have no resolved values or that may be out of scope due to noise, bad data, missing data, or other modeling reasons. These results may be undefined for many reasons and may be dropped from further prediction and analysis. In the case where prediction of zones cannot be accomplished, a simple median smoothing or strict substitution may be used to resolve the inconsistencies.

The program instructions executed in process block 2150 may be repeated one or more times until the program instructions of process block 2170 indicate that no small zones are identified in the set of crop response zones. The process may be repeated using different criteria, different parameters, or different parameter values. Small crop response zones that cannot be identified manually or by computer programming identification are passed to process block 2160 for further post-processing.

In process block 2160, a set of response zones is post-processed. Post-processing of the crop response zones may include eliminating the zones that are fragmented or unusable. The post-processing executed in process block 2160 may be repeated one or more times when further processing is identified by process block 2170 until the quality of created response zones is satisfactory. The process may be repeated using different criteria, different parameters, or different parameter values.

Metadata about the created response zones is generated and stored. Furthermore, a test may be performed to determine whether the process of delineating response zones needs to be repeated. If the delineation process is to be repeated, then further delineating of the response zones is identified by program instructions of process block 2170 and repeated by the program instructions of process block 2140.

The response zone delineation process is performed for different values of a response class. A response class refers to one or more areas in a farm and/or field that have relatively homogeneous crop-yield limiting factors. The areas are not restricted to a spatial continuity. For example, several response zones which are spatially separated from each other could belong to the same response class and could be operated or managed in the same manner.

Process block 2180 represents the repository for processed response zones that store the delineated pre- and post-processed data sets as identified and labeled as crop response zones. Crop response zones are categorized as clusters, for one or more of many geo-spatial boundary areas for each of the farms or fields. The characteristics of the stored crop response zones represented by the processed cluster characteristics and identified by the geographical zone boundaries may also be called ground types in the illustrative embodiment.

Figure 3A:
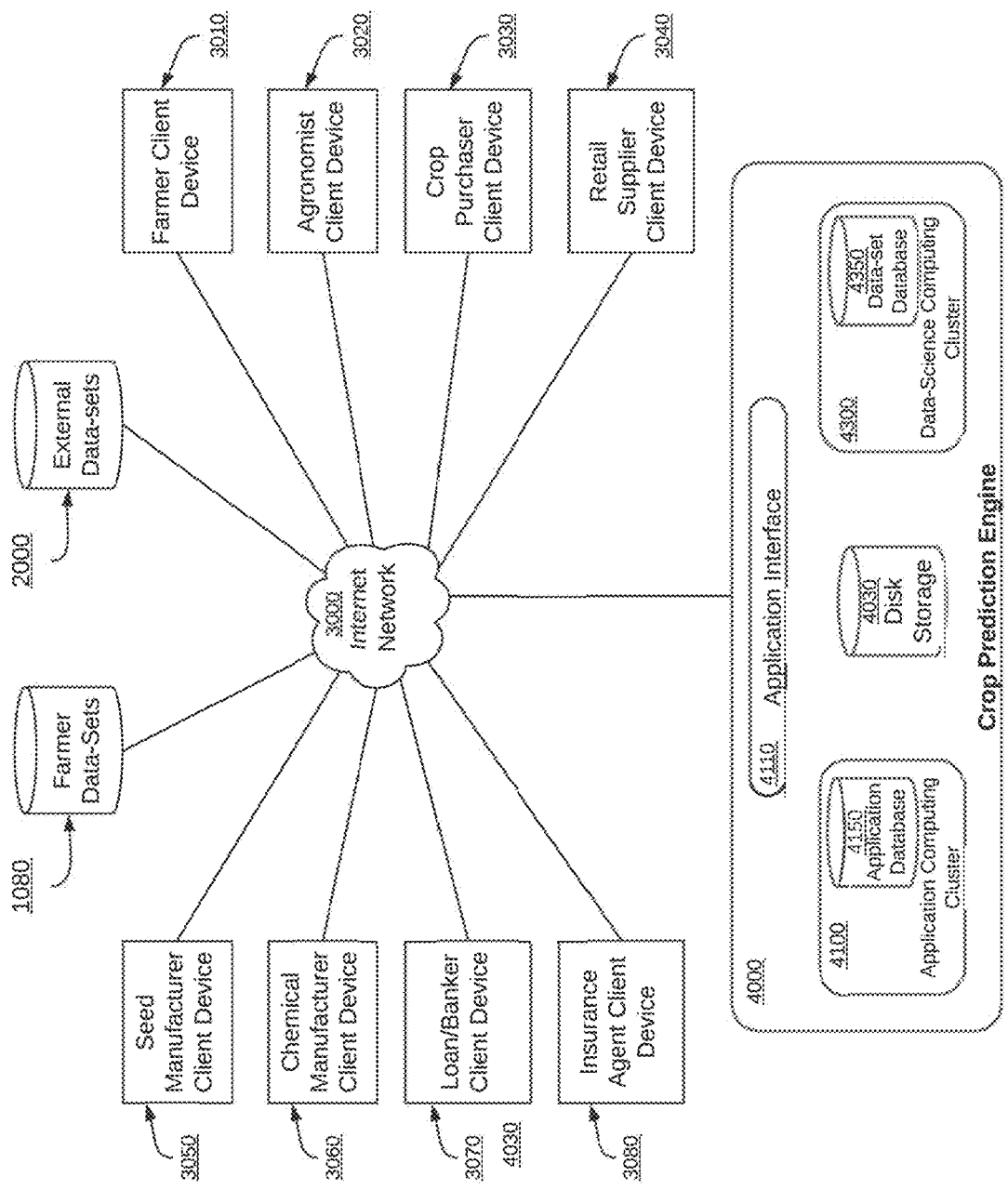
FIG. 3A shows an illustrative system having distributed client devices that interface with a crop prediction engine.

Referring to FIG. 3A there is shown an illustrative system having distributed client devices that interface with a crop prediction engine 4000. The illustrative system includes industry standard client devices such as desktops, notebooks, laptops, Android, and iOS mobile or stationary client devices.

Figure 4:
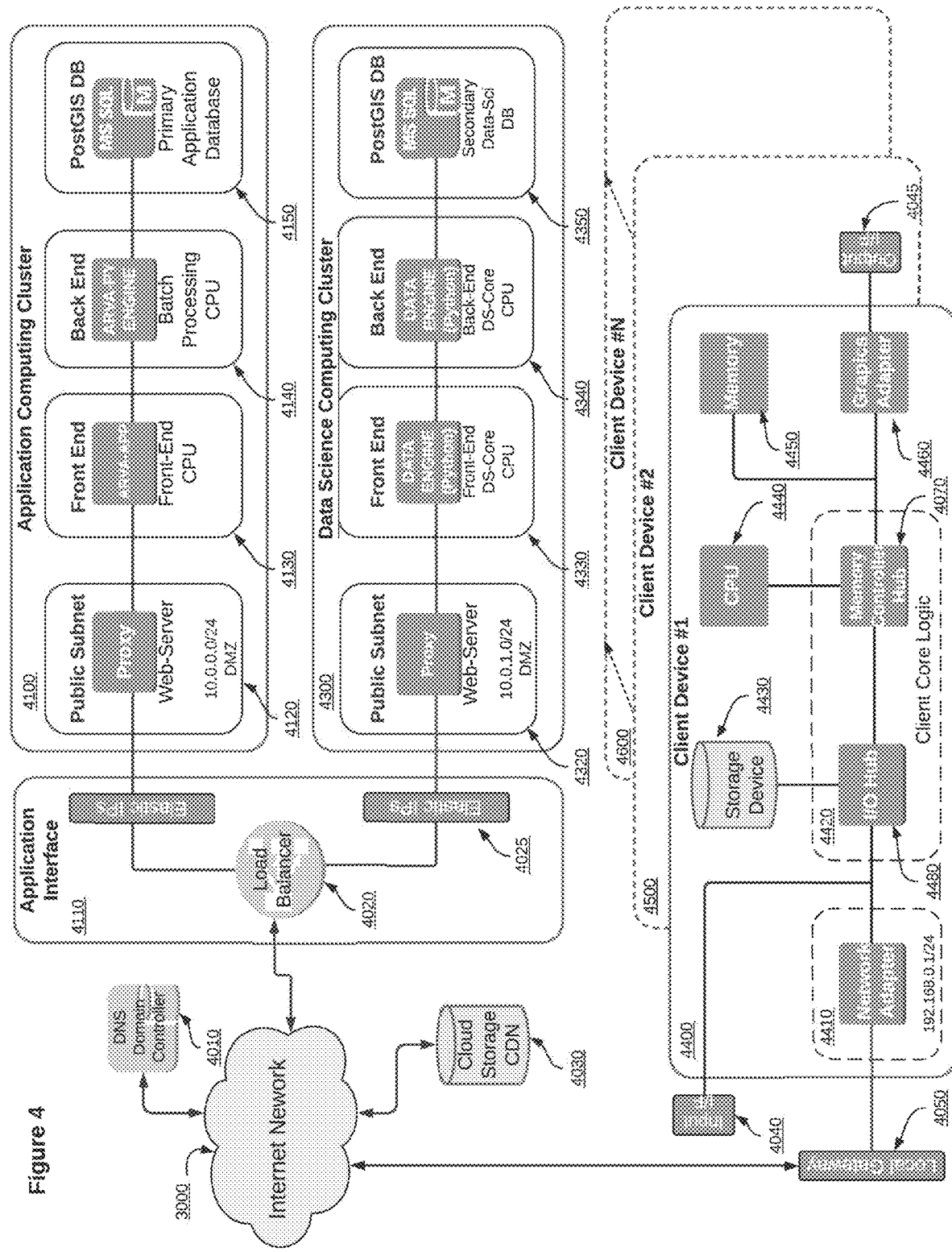
FIG. 4 shows an illustrative high-level diagram of networked computing systems.

In the illustrative embodiment one of more users upload data, issue commands, and retrieve results using one or more client devices 4400, 4500 and 4600 over the Internet 3000 to interface with program instructions running on both the client devices and the apparatus platform of the illustrative embodiment in FIG. 4. The program instructions running on the application computing cluster 4100 and the data science computing cluster 4300 form the backbone of the crop prediction engine 4000 used to predict crop yield.

The farmer data sets 1080 in FIG. 3A provide a representation of a storage device with programming instructions to store, send and receive various data sets stored by the farmer or the farmer's agronomist, consultants, suppliers, or other representatives that are typically local to the farm under management. In another embodiment the farmer data sets 1080 may be stored in remote storage maintained by the farmer's equipment suppliers, software vendors and/or consulting partners.

The external data sets 2000 in FIG. 3A include a representation of data sets provided by third-parties that are generally supplied for entire regions and may not be exclusive to a specific farm or field. These data sets may be from database servers or from permanent storage devices and may contain public or private data sets. Data sets from third-parties are typically accessed over the Internet but may also be acquired from direct storage devices on their respective host platforms.

In the illustrative embodiment, farmer data sets 1080 and external data sets 2000 are uploaded and/or queried remotely through at least one Internet 3000 network connection connected to the Application Interface 4110 by one or more computing apparatus running program instructions on one or more computing clusters 4100, 4300 or in one embodiment on at least one computing cluster and the crop prediction engine. The external data sets 2000 may represent stored and maintained non-farmer specific data. Non-farmer specific data may be data sets collected by sensors on farm equipment and/or sampling equipment local to the area where specific farm management is performed. The external data sets 2000 represent data sets that are typically stored in raster format from geographic regions where the feature set characteristics are typically remotely gathered for large portions of land. For example, external data sets 2000 may be from satellite, flight recordings, agriculture or government agencies and private companies that sell data sets and the like.

As used herein, a "portion of land" or "plot of land" refers to any amount of land in any shape or size. For instance, a "portion of land" can refer to a farmer's entire property, a field, a plot of land, a planting region, a zone or a crop response zone, and the like. Likewise, a portion of land can include one or more "sub-portions" of land, which refers to a subset of the portion of land of any shape or size. Various types and formats of data may be stored in the both the sensor data sets from the farmer 1080 and external data set 2000 for access by the other components of the crop prediction system 4000 performing one or more machine learning operations in order to train the crop prediction engine.

Prediction information from the system 4000 is used to predict crop production for a portion of land, and to assist in identifying one or more sets of farming operations including recommended applications like the addition of recommended nutrients and seed types to optimize crop production. For each of the farmer data sets 1080 and external data sets 2000 individual files of data may be stored as flat files, in columnar storage, in binary format, or other such formats that may be accessed via one or more storage devices, relational databases, columnar databases, NoSQL storage, horizontally scaled databases, and other such databases.

As used herein, the term "crop prediction engine" refers to a hardware component, e.g., a cloud based server, that implements one or more "machine learning prediction models" or a "prediction model" that uses one or more machine learning operations to predict a measure of crop production based on information including field information, or that is trained on information including field information using one or more machine learning operations. In the illustrative embodiment, the crop prediction engine generates a predicted measure of crop production.

By way of example and not of limitation, the crop prediction engine 4000 can be trained by any machine learning operation, such as those described herein, or any combination of machine learning operations for predictions of crop production.

The term "crop prediction information" refers to any measure that relates to expected crop production, such as crop yield, crop quality, crop value, or any other such suitable measure of crop production. Crop prediction information can also refer to a set of farming operations expected to result in the measure of expected crop production when performed in a specified manner, at a specified time/location, and the like.

"Field information" can include one or more of past and present crop production information, past and present geographic information, past and present agricultural information, past and present agronomic information, past and present sensor data associated with crop production, any other information related to the planting, growing, and harvesting of a crop, and any other field parameters as described herein.

Referring to FIG. 3A there is shown an illustrative system having distributed client devices that interface with a crop prediction engine 4000. In the illustrative system, the system includes at least one of the following client devices, namely, a farmer client device 3010, an agronomist client device 3020, a crop purchaser client device 3030, a retail supplier client device 3040, a seed manufacturer device 3050, a chemical manufacturer client device 3060, a banker client device 3070, and a crop insurance agent client device 3080.

Additionally, the system environment of FIG. 3A includes the crop prediction engine 4000 communicatively coupled to components that include application computing cluster 4100, disk storage 4030 and data science computing cluster 4300. Furthermore, the application computing cluster 4100 includes an application database 4150 and the data science computing cluster 4300 includes a data set database 4350.

As illustrated in FIG. 3A, the multi-dimensional input data sets represent the "features" of the environment that may be stored locally in disk storage 4030 or remotely stored in a data set store 1080 (shown in FIG. 1) or the input data sets may be represented more generally as a data set 2000 (shown in FIG. 3A). The feature data sets are input prior to any processing by the crop prediction engine 4000. The feature data sets may represent the raw input that after possible pre-processing and de-noising may form the independent variables used to train the crop prediction engine 4000.

The data sets generated from the various client devices and/or various data sets shown in FIG. 3A may be implemented within the same computing device or may be implemented in a mixed fashion between one or more different computing devices at one or more physical locations. In another embodiment, the network communication between a client device and the crop prediction engine 4000 may not only include the Internet 3000 but may be embodied as one or more private, public or VPN networks where one or more of the client devices of FIG. 3A are communicatively coupled to the crop prediction engine 4000.

In yet another illustrative embodiment, the crop prediction engine 4000 may be integrated with one or more client devices in a manner where the client devices of FIG. 3A communicate directly with each other and thus do not require a network connection to one or more remote crop prediction engines running on one or more remote computing clusters.

Referring to FIG. 4, there is shown an illustrative high-level process block diagram of networked computing systems. The networked computing systems include a client device 4400, which may be any device having computer functionality.

Client device types may include a mobile telephone, a smartphone, a tablet computer, a desktop computer, a laptop computer, a workstation, a personal digital assistant and may include smart farming equipment such as a smart tractor, smart harvester, smart planter, and fertilizer as-applied implements, including smart soil sampling and irrigation devices and the like. Other client devices may be embedded into unmanned vehicles, drones, or other aircraft and may be remotely controlled or be autonomous.

In the illustrative embodiment, client devices are configured to communicate with at least one crop prediction engine 4000 (shown in FIG. 3A) of the illustrative embodiment via the Internet 3000 or through one or more other network architectures using one or more different network protocols for data transport and communication. In such an embodiment, the communication is by device client via a web-browser interface but may also be of another method like an application programming interface (API), wired interface such as Universal Serial Bus (USB) or on a private network where a client device is typically accessed by a native operating system resident on a client device.

Referring back to FIG. 3A, the farmer client device 3010 may communicate with the crop prediction engine 4000 via the Internet network 3000 to upload farm related data sets collected by various smart farm equipment equipped with at least one computing device and Global Positioning Systems (GPS). Some uploaded information may be input to a client device manually by the user such as tilling or no tilling, irrigated or not, previous cover crop information, application of nutrients or pesticides by air, flat applications of manure, applications that do not have GPS, quantity and rate monitoring and other information that is not autonomously generated by smart farming equipment. Additionally, the farmer client device 3010 may be used to request and receive prediction information and recommendations such as predictions of crop production and recommendations of soil nutrients and seed products to apply to achieve a predicted or desired crop-yield.

The interactive communication of data sets and visualization between the farmer client 3010 and the crop prediction engine 4000 allows the farmer to optimize crop yield at lower application costs, allowing the farmer to identify farming operations that can optimize crop production and efficiency to improve the overall seasonal return on investment.

In another illustrative embodiment, the farmer's client device 3010 may be used to communicate with other client devices attached to the network through the application interface 4110. The communication between users of a client device and the crop prediction engine 4000 allows for acquisition of required supplies, negotiations for product costs and deliveries, planting and harvest scheduling, and expected crop-yield output based on farm management and application practices.

Thus, the illustrative crop prediction engine 4000 is configured to circumvent the delays and added expense of the historical practice illustrated in FIG. 1 by circumventing the typical retailer supply chain. Circumvention of standard retail purchase and delivery using the illustrative embodiment opens up options for the chemical manufacturer client device 3060 and seed manufacturer client device 3050 to sell directly to local farm management personnel.

For example, the crop prediction engine 4000 may prescribe nutrients, seeds or other farm management supplies and based on such predictions autonomously place purchase orders directly to manufacturers and suppliers. Additionally, a client device may be used to directly obtain bids from crop purchasers and/or crop brokers 3030 who can view estimated production volumes and prices directly. The prediction engine 4000 sources information by inputting data from multiple client devices and deriving the optimal soil and seed application costs for desired crop production in preparation for planting. This allows the farmer, agronomist, or crop consultant to rely on trained AI models to understand decisions between the multiplicity of soil and seed characteristics. Thus, recommendations for optimal crop efficiency with precision application may be obtained through the crop prediction engine 4000 described herein.

In the illustrative embodiment, the agronomist client device 3020 may communicate with the crop prediction engine 4000 via the Internet network 3000 to access both farm information collected by smart farming equipment and to access crop prediction information generated by the crop prediction engine 4000. When permission from the farmer is granted through the farmer client device 3010, data set information stored by the disk storage device 4030 may be downloaded through the agronomist client device 3020 interface. Other data sets provided by the agronomist may be uploaded over the Internet network 3000 to the crop prediction engine 4000 through the application interface 4110.

The agronomist may use recommendations from the system, modify those recommendations, upload data sets such as laboratory soil sample reports, field, or farm boundaries, known environmental variables, fertilizer and/or seed recommendations including prescriptions. The agronomist may also obtain market pricing based on crop-yield predictions from the crop prediction engine 4000.

Other information shared by the farmer with one or more agronomists and/or consultants may include information about farm management operations such as tilling or no tilling, irrigating or not irrigating, previous cover crop information and other information that is not autonomously generated by smart farming equipment. Additionally, the agronomist may request yield information stored in the crop prediction engine 4000 such as previous year's crop-yield results from harvest of specific farms or fields. The interactive communication of data sets and visualization between the agronomist client device 3020 and the crop prediction engine 4000 allows the agronomist to further recommend suggestions that may optimize crop yield at lower application costs, optimize crop production, and improve the farmers' overall seasonal return on investment.

In another embodiment the agronomist's or consultant's client device may be used to communicate with other client devices attached to the network 3000 through the application interface 4110. The communication between users of a client device through the application platform may be used for acquisition of required supplies, negotiations for product costs and deliveries, planting and harvest planning, expected crop-yield production, and return on investment based on farm management and farm and/or field application practices.

For example, the user of the agronomist client device 3020 can change the type of fertilizer to be applied, based on supply and demand, and can change the harvest data by moving the date based on expected weather changes. Thus, the agronomist through the agronomist client interface associated with agronomist client device 3020 can modify suggested farming operations as a result of the predictions from the crop prediction engine. The agronomist client device 3020 may also be the same as the retail supplier client device 3040 or the crop purchaser client device 3030 or the same for any other client device shown in FIG. 3A.

In the illustrative embodiment, the crop purchaser client device 3030 communicates with the crop prediction engine 4000 through the application interface 4110 via the Internet network 3000 to receive crop prediction information for future crop production in one or more portions of land. The purchaser, through the client device 3030 may send bids or purchase requests to secure purchase rights for estimated or actual crop harvests (for instance, sending bid contracts to the farmer client device 3010). The purchaser client device 3030 may be used by one or more crop-brokers or other crop recipients who have been granted permissions by the farmer to share or view farm projects that may include future or current harvest information predicted by the crop estimation engine 4000 on the application computing cluster 4100. For example, the purchaser through the purchaser client device 3030 may enter agreements to obtain from the farmer a portion or all of an expected crop harvest. Thus, the purchaser through the purchaser client device 3030 accesses the crop prediction engine 4000 via an interface 4110 that allows the user of the purchaser client device 3030 to identify predicted crop production information from one or more farmers who use one or more embodiments to automate the generation of crop acquisition agreements with the one or more prospective crop purchasers. A crop purchaser (crop recipient) may receive a harvested crop directly from a farmer or from the farmer through a crop broker.

The crop purchaser client device 3030 communicates with the crop prediction engine 4000 via the Internet network 3000 to receive information via the application computing cluster 4100. For example, corporate users may have one or more registered farmers, brokers or consultants registered in a corporate organizational account such that any corporate user of a crop purchaser client device 3030 may identify expected crop production of one or more farmers, including the crop type and expected crop production quantities of the crops produced by one or more farmers. In one embodiment the application computing cluster 4100 may include shared farmer accounts, agronomist accounts, consultant accounts or customized projects supported by the crop prediction engine 4000. For example, the accounts can be from a group of farmers in a single location, multiple locations, from a geographical region or a corporate division. A corporate user of the crop purchaser client device 3030 can use this information to enter into crop acquisition agreements with one or more farmers or one or more brokers or one or more crop recipients.

In the illustrative embodiment, the retail supplier uses one or more client devices 3040 to communicate with the crop prediction engine 4000 through the application interface 4110 via the Internet network 3000 to send and receive information about farm management operations, supplies and services for historical, current, or future crop production relating to one or more portions of land. Typical use of the crop prediction engine, between farmers and retail suppliers, may be for acquisition and scheduling of supplies and services that may be based on the estimations and recommendations from the system's crop prediction engine 4000.

For example, the user of retail supplier client device 3040 may be an agriculture co-op, farm supply company or seed and fertilizer retailer who has been granted permissions by the farmer or corporate vendor or partner to view crop prediction engine projects that may include farm chemical and seed application requirements and harvest information that are created or stored on the application computing cluster 4100. The retail supplier through the retail supplier client device 3040 may enter into agreements to obtain information and requests from one or more farmers or enter into alternate agreements with alternate requests from corporate suppliers through one or more other client devices illustrated by blocks 3050, 3060 and 3070 of FIG. 3A. Information transfer between farmer client devices 3010 and retail supplier client devices 3040 with other client device users may relate to client requests like farmer requests for retail services or agronomist services through client device 3020, or requests for other supplies or services through any other client devices. The retail supplier client device may also be used to share logistics and order information with other manufacturers such as seed manufacturers through client device 3050 and chemical manufactures through client device 3060.

In another embodiment the retail supplier client device 3040 may be used for logistics for purchase and delivery of fertilizers, pesticides and seeds as required by the retail supplier's farming clients, agriculture consultants or agronomists. For example, corporate users may have one or more registered retail suppliers registered in a corporate organizational account, such that any corporate user of at least one of the retail supplier client devices 3040 may identify expected farm management and crop production requirements of one or more retail suppliers. A corporate user of the retail supplier client device 3040 can use the crop prediction engine 4000 and associated crop prediction information to enter into crop acquisition agreements with one or more manufacturer, supplier, farmer, agronomists, or any combination thereof. Thus, based on information in farming projects shared by one or more client devices with the retail supplier client device 3040, the retail supplier may be contracted through the illustrative embodiment for supplies and services provided by the retail supplier.

Figure 3B:
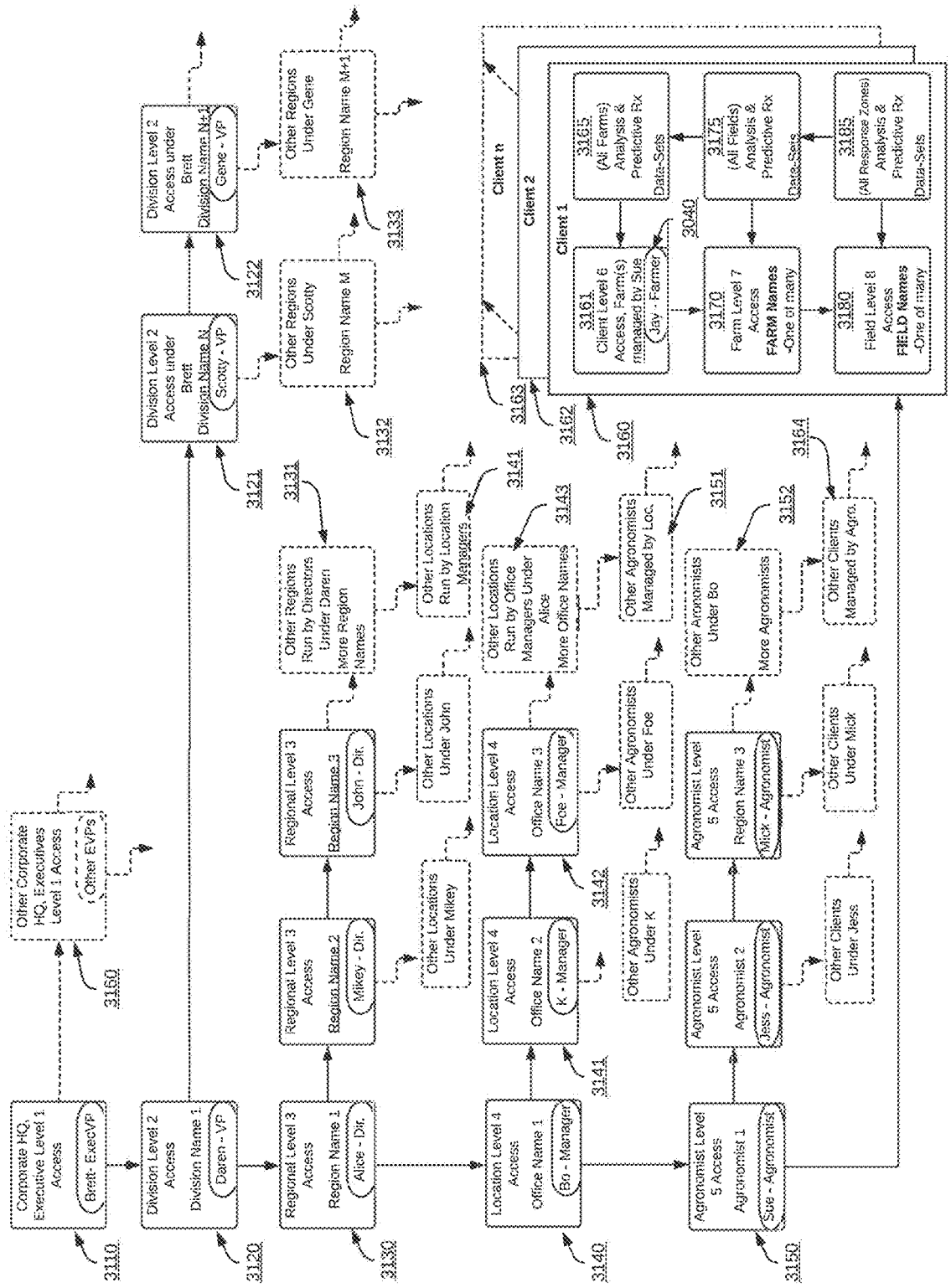
FIG. 3B shows an illustrative system that supports access levels within corporate management in a typical organizational hierarchy.

The seed suppliers or manufacturers, chemical or fertilizer manufacturers, loan officers or bankers, and crop insurance agents, hereafter called the "corporate users," may be considered corporate suppliers of products and services sold, leased, or licensed that communicate through their respective client devices as represented in FIG. 3A by client devices 3050, 3060, 3070 and 3080. The use of the crop prediction engine 4000 by corporate users is similar to the use and operation of the system by the crop purchaser through a client device 3030. Corporate users may have corporate accounts and levels of access as illustrated in FIG. 3B. Corporate users may also communicate and share projects with retailer clients, agronomist clients, consultant clients, and farm clients (hereafter called "local clients") through local client devices 3010, 3020, 3030 and 3040 connected to a network such as the Internet network 3000.

The crop prediction engine 4000 includes an application interface 4110 which includes programming instructions for the network interface. The application interface 4110 is the connection to one or more networks used for the transfer of information between the client devices and the crop prediction engine 4000. The application computing cluster 4100 includes the computing components to manage the client's computation and storage requirements. In one embodiment, the application computing cluster 4100 and the data science computing cluster 4300 may be the same components with a single computing cluster and database structure for both. In the illustrative embodiment, the data science computing cluster 4300 and related data set database 4350 are used to perform various operations described herein.

The crop prediction engine 4000 receives data from various sources including, but not limited to, a corporate user, data set types, local sensor data sources, and other such data sources to perform machine learning operations on the received data produced by one or more crop prediction models. The crop prediction engine 4000 has the ability to predict and recommend precision application of chemicals, seed types including seed genetics and recommended amounts and rates of farm and/or field application. The data from these data set sources, which may also be referred to interchangeably as "features," can be combined into a feature-set that may be extracted from the combined data and used as training data to support crop prediction models spanning different temporal systems, different spatial coordinate systems, and different measurement systems.

For example, sensor data streams can be a time series of scalar values linked to a specific latitude/longitude coordinate system. Similarly, LiDAR data can be an array of scalar elevation values on a 10 meter rectangular coordinate system, and satellite imagery can be spatial aggregates of bands of wavelengths within specific geographic boundaries. After aggregating and standardizing data from these data streams in a universal coordinate system, such as the UTM reference system, feature sets can be extracted and combined. For example, feature sets that can be extracted and combined include a soil wetness index from raw elevation data, or cumulative growing degree days from crop types and planting dates.

"Crop quality" can refer to any aspect of a crop that adds value to a farmer, crop purchaser or crop recipient. The various possibilities for crop quality and crop quantity inferences can be large. In general, crop quality may refer to physical or chemical attributes of any particular crop. For example, there are many different attributes that are related to a particular crop, namely, a genetic trait, a modification, an epigenetic signature, moisture, protein, carbohydrate, ash, fiber, fat, oil, color, whiteness, weight, transparency, hardness, presence of foreign matter, absorption, milling degree, kernel size or volume distribution, grain length or breadth, density, broken kernels, stress cracks, immature grains, measurements and measurement expectations for gluten, sodium dodecyl sulfate, sedimentation, toxin levels, molds, insects, or other material damage and attributes related to crop quality.

Crop quality may also be inferred from the maturity or growth stage of a crop, the storage of a harvested crop (e.g., the type of storage: bin, bag, pile, in-field, box, tank, other containerization), the environmental conditions (e.g., temperature, light, moisture/relative humidity, presence of pests, $CO_2$ levels) which the crop encountered during storage, crop preservation (e.g., freezing, drying, chemically treating), or a function of the length of storage time.

In another embodiment the food grade quality may be inferred from the variety of plant, damage levels, soil chemistry or one or more production practices used to grow the plant. In some embodiments, crop quality is a calculated, derived, inferred, or subjective classification based on one or more measured or observed physical or chemical attribute of a crop, or a farming operation used in its production. In other embodiments, one or more quality metric is collected, measured, or observed during harvest. For example, dry matter content of corn may be measured using near-infrared spectroscopy on a combine. In yet another embodiment, a quality metric is a grading or certification by an organization or agency, for example grading or certification by the USDA, organic or non-GMO certifications.

The system of FIG. 3A allows users to name at least one "project," share at least one project having viewing rights and/or editing rights with other client device users. The access may be provided from at least one client device having a client browser that is communicatively coupled to the Internet 3000. In the illustrative embodiment, "projects" are set up and managed by users and contain information such as data sets, features, predictions, and ROI estimations for one or more plots of land. The projects may contain information for any access levels where the user has permission as illustrated and outlined in FIG. 3B.

Referring to FIG. 3B there is shown an illustrative system that supports access levels within corporate management in a typical organizational hierarchy. The illustrative system in FIG. 3B includes eight possible levels of organization, in which the hierarchy assigned to each of the eight levels and the respective access privileges for each level is shown. In one embodiment the application administration interface is initially used to set-up one or more corporations to follow one or more of the active organizational hierarchy levels out of the eight possible levels. In another embodiment there may be more or less than eight levels set-up by the administration user interface software. In yet another embodiment the corporate names assigned to each level may be the actual usernames assigned to each account holder and names may be set by the organization name custom to the user account for each level. Names of the organizational hierarchy may be set by the administration interface or by the root user (or root users) assigned to the corporation during initial set-up of the main account. Set-up of the main account, the number of levels, the usernames per level and the organizational level name is typically performed by the application administrative interface of the crop prediction engine. In another embodiment where the root user is a single sole-proprietor of any company or entity, the term corporate user may not apply. For the purpose of this specification, a single root user may also be referred to as "a corporate user" in the context of a single level of the organizational hierarchy.

In FIG. 3B the top level of access of the organizational hierarchy is called the "Corporate HQ Executive" level 3110 which has level-1 (highest) access privileges and may be considered the highest level of the organizational hierarchy as outlined in the present hierarchy template. The users with level-1 privileges can view and access not only information from their own account but in addition any user account, including all the information within the account below this user level. For example, from block 3110, the indicated EVP "Bret" can view all the projects, see crop prediction reports, establish return on investments, determine correspondences or any other information for system access levels 2 through 8, i.e., any access level below Bret's access level. In another embodiment any number of additional corporate HQ executives 3160 may be added to the organization by the system administrator or by the root user assigned to that access level of the illustrative software application platform.

The organizational hierarchy and assigned names continue for the levels selected by the administration users under advisement from the corporate root user for the remaining assigned levels of the organization. For example, Level-2 accessors 3120, 3121 and 3122 may be assigned level-2 access privileges in the overall organizational hierarchy. In the example diagram of FIG. 3B, block 3120 illustrates a possible configuration of the division level access that has been granted to level-2 root user Daren. For example, in addition to assigning Daren 3120 as the root user for this division, an individual division name that fits the nomenclature of the corporation's organization names may be assigned in the organizational hierarchy template under "division name 1" as illustrated in FIG. 3B. Blocks 3131 and 3122 and other level-2 division managers (Vice presidents Scotty and Gene, for the purpose of this example) may also be assigned to the corporate organizational hierarchy.

The assignment of users in the organizational hierarchy of FIG. 3B continues to the assignment of regional directors as indicated in blocks 3130-3133. In one embodiment regional directors are granted level-3 access and manage one or more locations 3140-3141. In the illustrative embodiment, the levels of assigned hierarchy may continue as needed by the corporation filling out the organizational hierarchy as needed for one or more particular corporation levels.

For example, regional director Alice manages at least four locations run by location office managers Bo 3140, K 3141, Foe 3142, and other additional location office managers 3143. The location office managers may not see reports, predictions or crop production results for each other without explicitly granting permissions to share projects that contain information from lower levels (i.e. levels 4-8) with each other. Although because Alice is the regional director, she has the privileged access to see projects and information for all the locations and corresponding location office managers under her management from the agronomist/consultant level-5 3150-3152 down through the client (Farmer) level-6 3161, the client (Farm) level-7 3170, and on to the client (Field) level-8. Alice may run reports, do ROI analysis, and use any of the application system features on one or all of the locations she manages.

In one embodiment, levels of the corporation such as the agronomist level-5 may not exist in the corporate organizational hierarchy. In this case level-5 may be pulled out and the organizational hierarchy would apply the next level (level-6), the client level, as the next access level in the organization. As a further example, the organizational levels may be collapsed, again referring to FIG. 3B, if Sue 3150 is the agronomist assigned to Bo 3140 for the office location "name 1" she may be responsible for recommendations and application prescriptions to client-1 3160.

In the illustrative embodiment the client with level-6 access is typically the farmer or landowner who has at least one farm under management. When the hierarchy has more than one farm under one client, the organizational hierarchy may assign at least one farm, with access level-7, to the organizational hierarchy 3170. In the illustrative embodiment, there is no fixed indication that all levels in the organizational hierarchy work for the level above them. For example, not all levels are always corporate employees working for the same corporation and may be independent organizations in separate businesses as needed for supply and demand by contract, agreement, or license between parties at different hierarchical levels and may be set up as independent businesses from other levels within the hierarchy.

In FIG. 3B, the organizational hierarchy may have multiple clients assigned per location or agronomist working in a location indicated in blocks 3160, 3162 and 3163. In the illustrative embodiment, each client of the organizational structure has at least one farm under management as indicated in block 3170, in which each farm has at least one field 3180 within its boundaries and within each field are subfields that make up the different crop response zones 3185 that may provide one or more feature data set used to train the crop prediction models as described in the illustrative embodiment.

In the illustrative embodiment, the crop prediction engine 4000 provides recommendations, predictions, and analysis data 3165, 3175 and 3185 to each of the respective levels 3161, 3170 and 3180. Additionally, the crop prediction engine 4000 may provide recommendations, predictions, and analysis to other levels 3110, 3120, 3130, 3140 and 3150 to improve farm production effectiveness, and corporate ROI while reducing operational risks for the entire hierarchy of organizations.

For example, Jay is the farmer indicated in block 3160 with multiple farms under management 3161 having level-6 access to each of the farms 3170 of level-7. Jay may contract with a retail supplier through the retail supplier client device 3040 for the application of fertilizer to one or more farms 3170 under Jay's management. Jay may grant access to a single retail supplier by sharing a project that contains only the details of a single farm with one or more fields where the fertilizer application is to take place.

In the illustrative embodiment, separate projects or organizational nodes may be set up by administrative users at any level of the organizational hierarchy tree. For the purpose of illustration, Projects and Organizational Nodes (Org-nodes) may be synonymous to each other and have the same definition. To further exemplify this, Jay may set one or more projects containing specific information to be shared with any other level within or outside of the organizational hierarchy by giving specific access to Jay's farm/field projects. Any users in the system can see what projects are shared with them and what projects have been shared to them by other users. Projects may be set with view only or edit/view authority (use rights) but only by the project owner that shares the projects. In the privacy and ownership terms and conditions any one level when sharing is giving view and use rights to the other level but, no ownership rights to the actual data shared.

In one embodiment, sharing project information with third parties within or outside the organizational hierarchy may have a billing and commerce component and client device interface, in which account credits may be purchased and subsequently used to gain access to shared information and reports produced by the crop prediction engine and any other associated platform components or functionality. Access levels based on shared information and account credits may be set by each level or a single level of the organizational hierarchy or by the owners or its affiliates who sell or license the platform or a version of the platform for its commercial use.

Referring to FIG. 4 there is shown an illustrative high-level block diagram of networked computing systems. The physical components may be separated into one or more client devices 4400, 4500 and 4600 and include the associated computing components to receive and transfer data through local gateway 4050, the Internet network 3000, DNS domain controller 4010 and application interface 4110. The client devices interface with clusters of computing components and cloud storage device 4030, application computing cluster 4100 and data science computer cluster 4300.

The physical components of a typical computing client device 4400 are used for data set transfer, input/output, and visualization through Internet 3000 to one or more storage devices 4030 or one or more computing clusters to view outputs from the crop prediction engine 4000. The outputs are viewed on at least one of a display device, monitor, CRT, or the like, through one or more VGA, DVI or the like, output 4045 interfaces. Computing client device 4400 includes at least one main memory subsystem 4450 including Random Access Memory (RAM) a volatile memory or Non-Volatile Random Access Memory (NVRAM) for storing information and instructions to be executed by processor 4440 through at least one bus or other communication mechanism for communicating information between the physical components on the client device 4400.

The client device 4400 may include at least one interface connecting input/output (I/O) peripheral devices 4040 like keyboard, mouse, or touch screen to input user actions and requests into the client device for further processing by the system. The I/O hub may be connected to one or more buses to control at least one Universal Serial Bus (USB) used for connection to external devices and other peripheral devices. The client device 4400 has at least one hardware processor (CPU) 4440 coupled with one or more buses for processing information. The hardware processor may be a dedicated custom CPU or a general purpose CPU. The computer client device of block 4400 may also include core logic 4420 having a hardware I/O hub used to communicate between local storage device 4430, input peripherals 4400, network adapter 4410 and at least one memory controller hub 4070 connected between at least one processor and at least one memory device 4450 and at least one graphics adapter 4460 for graphical output, connected to at least one graphical display device for display of information and data visualization. The network adapter 4410 may be connected to an external Local gateway 4050 used to interface to one or more local and/or wide area networks like the Internet Network 3000 as needed for network communication. The network communications occur between at least one client device, other client devices and to other physical components such as the application interface 4110, one or more DNS controller devices or remote storage such as a content delivery network (CDN), cloud attached storage or dedicated storage subsystems 4030 as illustrated in FIG. 4.

Application interface 4110 may be used to communicate with one or more computing clusters via external networks like the Internet network 3000, dedicated storage 4030 and the DNS domain controller 4010. The application interface 4110 of the crop prediction engine 4000 interfaces through one or more busses to a load balancer 4020 that is dedicated to balance traffic between separate computing instances located within one or more computing clusters. Communications between the load balancer 4020 and the computing clusters may be through one or more elastic IPs 4025 allowing virtual dynamic reconfiguration of data routing between physical devices within one or more computing clusters.

Application computing cluster 4100 may be dynamically scalable for configurations that require the addition or removal of one or more computing instances and storage resources within the cluster 4100. In the illustrative embodiment, the application computing cluster 4100 includes at least one web-server associated with instance 4120 that may act as a network proxy for access and cluster communication with client devices running web-browser interface software. The application computing cluster 4100 may also include at least one front-end computing instance 4130 for processing main-line application program instructions originating from one or more external client devices 4400, 4500 and 4600. Additionally, the application computing cluster may include at least one back-end computing instance 4140 for back-ground computation of subroutines used to assist special operations. In the illustrative embodiment, the back-end computing instance 4140 may be one type of GPU or Math computing engine to assist and offload the computation requirements of the crop prediction engine. Furthermore, the application computing cluster may include having each of the computing instances 4120, 4130 and 4140 connected through one or more client device busses to at least one primary application database illustrated by block 4150.

In the illustrative embodiment of the crop prediction engine 4000, the database 4150 is configured as a geo-spatial database such as a PostGIS database that includes a Postgres database structure with geo-spatial extensions. In the illustrative embodiment, the geo-spatial database enables faster geographical based search, query and join operations that are typical in the geography referenced precision agriculture industry. Data sets of independent input variables and resulting dependent output variables are indexed and reference quickly in a geo-spatial database architecture based on unified GPS coordinates stored within the database. Other types of databases such as centralized, distributed, relational, columnar, hierarchical, NoSQL and the like may also be used for the primary application database for data storage, search, retrieval, and data association purposes.

The primary application database 4150 may be used to hold previously processed results computed from the pre-processing, scaling and normalization program instructions. Additionally, database 4150 may also store the predicted results from one or more prediction engine models. Furthermore, the database of 4150 may or may not be used for the database's geo-spatial extensions but may be used to store user account application information, account access levels and privileges, as well as stored references and default settings from universities, government agencies and the agricultural community.

In one embodiment the database 4150 of the application computing cluster 4100 may store the calculated predictive yield and application recommendations of the crop prediction engine used for map data visualization, return on investment calculations and recommendations for the amounts and rates of various seeds and nutrient products applied. Additionally, the primary application database 4150 may store and retrieve user account information to and from the primary application database. In one embodiment the primary application database 4150 may store and retrieve default information input through the browser based device client by application or administration users. In other embodiments, the application database 4150 may store and retrieve information from an external source such as an application programming interface (API) running on both a device client 4400 and one or more of the front end 4130 or back end 4140 computing cluster instances through the application interface 4110. Thus, in the illustrative embodiment, the system of FIG. 4 may store and retrieve data to and from at least one device client 4400 and at least one computing cluster 4100.

In an alternate embodiment, the Application Computing Cluster 4100 and the Data Science Computing Cluster 4300 may be combined into a single computing cluster with at least one application database.

In another embodiment, additional computing clusters such as the data-science computing cluster 4300 may be used as the physical components for computing to train and build the ML application for the crop prediction engine 4000. Cluster 4300 may contain the same physical components as that described above for the application computing cluster 4100 but run alternate software that is more specific to the task of ML research and development. In the illustrative embodiment, the data science cluster 4300 may be used by third parties to perform customizations as required by the systems users. Thus, the embodiment of the illustrative system uses the one or more of the physical components outlined in FIG. 4 to run and compute the system application as further defined below.

Artificial Intelligence has been used for agricultural prediction through modeling. Popular statistical and machine-learning methods for detecting interactions may include decision trees and their ensembles, random forests (RFs), node harvest, forest garrote, rulefit3, as well as other methods more specific to soil and environmental characteristics with categorical input features such as logic regression and multifactor dimensionality reduction. Historical tree-based procedures grow shallow trees to prevent overfitting of the data. Shallow trees exclude the possibilities of high-order interaction detection without predictive accuracy.

In the crop prediction engine 4000, random forests are used to circumvent these historical limitations. The use of random forests leverages high-order interactions to obtain high prediction precision and accuracy, with the exception that RFs alone do not support the interpretation of feature interactions in the resulting tree ensembles.

The illustrative embodiment of the crop prediction engine 4000 uses an RF training model to search for stable, high-order interactions by introducing an iterative process that sequentially grows feature-weighted RFs to perform soft dimension reduction of the input feature space to stabilize decision paths.

The crop prediction engine 4000 supports higher-order input feature combinations that are the most prevalent as they traverse through the RF decision paths of the tree from root to leaf. In addition to the prevalence identification, the higher predictive accuracy of the RF decision trees may capture more of the underlying soil and environmental attributes that lead to insights for chemical combinational interactions that may limit or pronounce crop-yield production for farmers. The crop prediction engine may determine a small subset or a single main feature input that contributes most to crop productivity. In the illustrative embodiment, the invariance of decision trees to monotone transformations mitigates some pre-processing requirements, which is known to be a main component of achieving normalization of the of feature data sets.

Due to the size, variability and lack of good signal-to-noise ratios found in most raw agricultural data sets, data normalization issues are a major concern in analysis and in the ability to achieve a stable agricultural prediction. The illustrative embodiment achieves improved predictive accuracy and extracts both known and compelling soil and environmental candidate interactions that derive one or more "Prevalence Differentials" that enable a predictive yield response.

In the illustrative embodiment, the crop prediction engine 4000 includes at least three basic steps to search for high-order feature interactions. Firstly, use of input data set feature re-weighting to adaptively regularize the random forest fitting. Secondly, the extraction of decision rules out of the re-weighted random forest, mapping from continuous or categorical into binary features. Thirdly, an ML bagging step that recovers the stable interactions with respect to boot-strap perturbation of the binary features.

In the illustrative embodiment, the crop prediction engine 4000 builds on a generalization formula of the Random Intersection Tree (RIT) training model. RIT performs a randomized search for high-order interactions among binary data set features in a deterministic setting. In the illustrative embodiment, RIT searches for co-occurring collections of s binary features of order S interactions that appear with greater frequency in a given class "C." The illustrative RIT training model allows for precise recovery of such interactions with a high probability with substantially lower computational effort.

Figure 5:
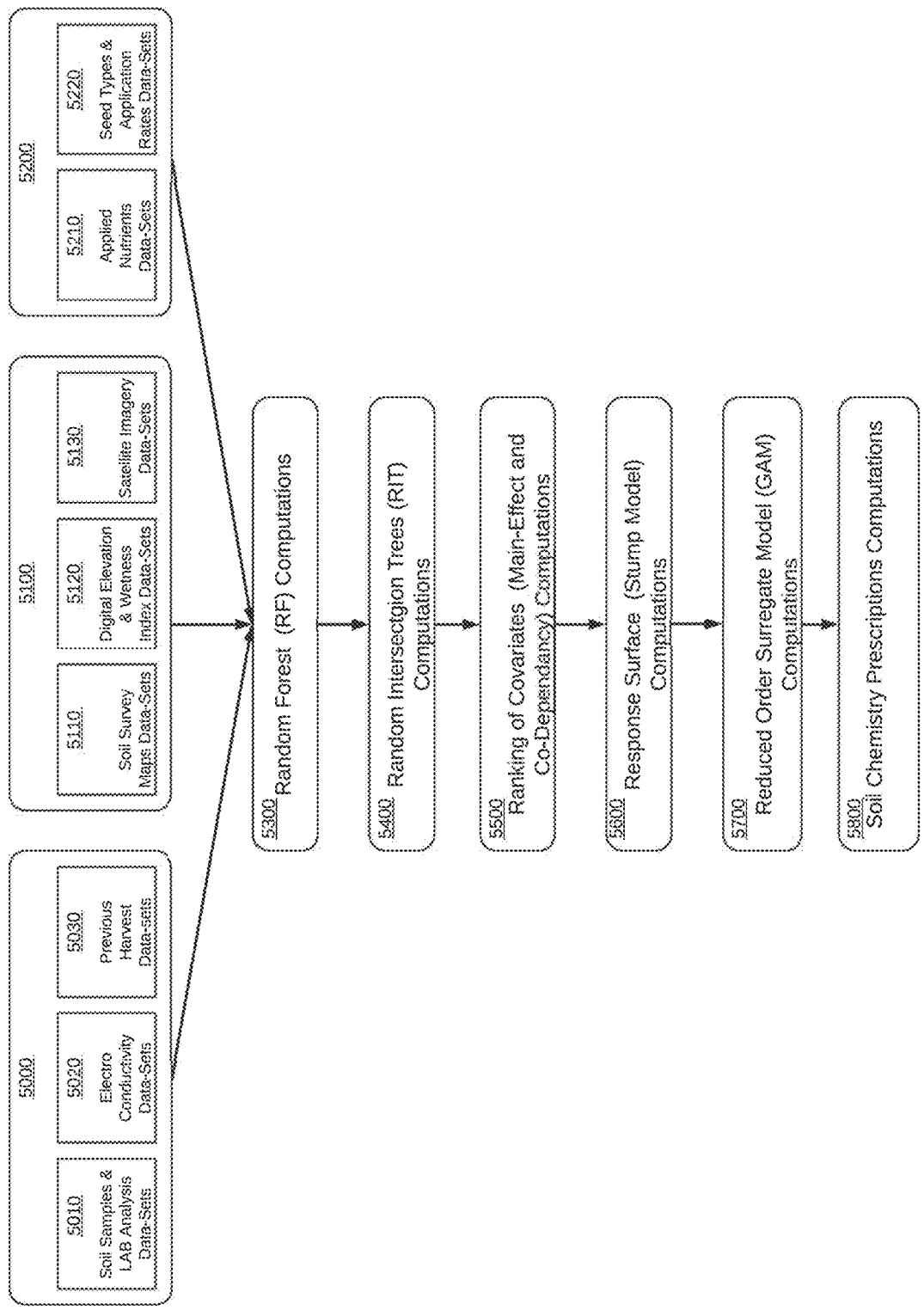
FIG. 5 shows an illustrative flowchart of the operations performed by a crop prediction engine, which is used to train a machine learning model.

Referring to FIG. 5 there is shown an illustrative flowchart of the operations performed by a crop prediction engine 4000, which uses machine learning processes. FIG. 5 summarizes the program instructions by grouping the program instructions into process blocks that are used by the crop prediction engine 4000 to predict a crop yield. More specifically, the process blocks 5000-5800 represent program instructions for receiving a multiplicity of data sets and the computational processing of those data sets in the illustrative method of the present embodiment to predict a crop yield from at least one trained ML model. Firstly, data sets are loaded to the permanent storage 4030 associated with data set process blocks 5000, 5100 and 5200 for pre-processing to identify covariates that are used to train the crop prediction engine 4000.

In the illustrative embodiment, data sets are ingested by the crop prediction engine through application client devices 4400, 4500 and 4600 (shown in FIG. 4) and client devices 3010 to 3080 (shown in FIG. 3A) by the program instructions associated with the crop prediction engine application software. Data sets are typically uploaded from the local storage, attached or removable storage at the local client devices. Client devices are typically connected through the Internet gateway 3000 to the illustrative cloud storage 4030 as described above.

The process blocks 5300, 5400, 5500, 5600, 5700 and 5800 are associated with operations performed by the crop prediction engine 4000. In the illustrative embodiment, the data-science computing cluster 4300 (shown in FIG. 3A and FIG. 4) may also be used for processing the program instructions within each process block. In another embodiment one or both of the application computing cluster 4100 (shown in FIG. 3A and FIG. 4) and data science computing cluster 4300 may be used to process program instructions within the process blocks shown in FIG. 5.

Referring again to FIG. 5, process block 5000 represents the ingested files from field or equipment sensors that contain a multiplicity of information in multi-dimensional data sets, farm feature sets or farm data features and the like hereafter referred to as "sensor data." Process block 5000 includes imported sensor data such as lab results 5010 from soil samples that are site specific. The soil sample results may be in the form of text files, like PDF's or CSV format and typically contain values for the soil chemistry at each sample location. Soil sample locations may be identified by GPS coordinates or by field name embedded within the file or by manual identification and may depend on the sample site locations and sampling resolution.

Sensor data from electro-conductivity 5020 measurements may be uploaded as additional data set information may be used during computations as an indication of the Organic Matter (OM) of the soil located in at least one site. In one embodiment, soil texture data may also be uploaded, again as supplemental information generated as an additional farm feature set. Electro-conductivity data files may be continuous, point or area sampled and will most likely contain GPS positioning for each value within the sensor data set. File formats for electro-conductivity may be in text, CSV, PDF, or shape file format as well as other forms including manufacturer specific or custom formats. Additionally, previous yield or harvest uploaded data sets 5030 play an important part in training the model of the crop prediction engine 4000.

In the illustrative embodiment, more than a single harvest of yield data is uploaded and stored for further computational analysis. Yield sensor data is typically collected automatically by harvester equipment using GPS position monitors, moisture sensors and elevation sensors and is typically collected in crop rows at the rate from one (1) to five (5) Hertz. Yield harvest upload files are typically noisy and dense data sets and may be in a shape file, CSV, or custom formats. In one embodiment, yield information may be a polygonal section where the yield is averaged and smoothed within the polygonal area as a single sample. Typically, the polygonal area is represented in one or more file formats as one sample per polygonal area of the harvest. In another embodiment the polygonal area per yield sample may be computed by the product of the harvester arm width, the speed of the harvester divided by the harvester sample rate in Hertz.

With respect to process block 5100, the ingested files from third parties such as government agencies, commercial companies, and agricultural groups, hereafter called "third-party" data sets, typically have been pre-processed to remove missing data and noise. However, the third party data sets may be in raw format and be unprocessed. Third party data sets in process block 5100 may vary in data format including raster, point, polygon, and multi-polygon and may need to be adjusted to a common coordinate system to align physically with other data feature sets. While sensor data sets 5000 are site specific and typically collected by sensors from farming equipment, the third-party data sets indicated in process block 5100 may span vast geometries covered by large data sets collected over time or from satellites that update weekly or even daily. The illustrative embodiment may use APIs to pull data into storage 4030, into the application computing cluster 4100 or data science computing cluster 4300 for processing and database categorization and use. Data sets represented by process block 5000 and 5100 may be in a variety of file formats and may be converted to other file formats prior to the computational purposes of the crop prediction engine.

At process block 5200 the data sets from data sensors originated by farm equipment and used for the application of fertilizers and seeds are uploaded. Planting data 5200 may be recorded by the programmatic interfaces. The planting data may include GPS tracking, seed-type or product selection, planting depth and planting rate in seeds per second or seeds per acre. Planting records are dynamically recorded and saved for uploading as a feature set for processing by the crop prediction engine 4000. The crop prediction engine may use seed variety, like genomic, hybrid, non-genomic, or custom seeds with special coatings or other traits to determine the seed types that are most cost-effective for crop production and have the best yield response in different soil chemistries or environmentally based clusters within one or more plots of land as identified.

Applied nutrient data sets 5210, typically fertilizers, may be applied from a programmatic interface that selects fertilizer product and application rate according to precise location information provided by GPS coordinates. In one embodiment, the programmatic interface relates to the application of such fertilizer products, GPS records, fertilizer product type and application rate. The sensor data is typically saved into one or more data-files as the products are being applied to one or more plots of land like fields. The saved data files are then uploaded and saved as a feature set for processing by the crop prediction engine 4000. Applied nutrient data sets 5210 may also be manually input. Illustrative data sets that would be manually input include fly over nutrient applications, blanket manure applications and other nutrient applications that are manually input and typically have positional relationships to fields and possible sub-fields. Seed types and application rate data sets 5220 may also be communicated to the crop prediction engine model.

Process block 5000, process block 5100, and process block 5200 represent program instructions to upload, process and store input data sets, which are multi-dimensional feature sets, to determine the overall dimension and/or order of computing required by the crop prediction model 4000. Note, the feature sets used to train the ML model may require pre-processing for noise reduction, averaging and coordinate system unification.

At process block 5300, program instructions representing an illustrative training model are used by the crop prediction engine 4000. In the illustrative embodiment, a random forest (RF) training model is implemented as a computational model. In operation, each of the RF trees is built into a set of tree estimators and calibrated using first out-of-bag training data, which assesses initial conditions, parameter settings, and first pass model quality using techniques like R-squared error minimization prior to application of actual training data sets. Tuning of the RF training model may be iterative and may use different feature weights based on the desired properties inherent to the set of training data as known to one skilled in the art. Once the RF training model has been tuned, a data set of multi-dimensional set of features is applied to each tree in the random forest.

Note the distinction between an "algorithm" and a "training model" for machine learning purposes, which are described in this patent. For purposes of this patent, an algorithm is derived by statisticians and mathematicians for a particular task. Thus, in machine learning, algorithms have already been derived. When an algorithm is implemented as machine code in a computer, the algorithm's utility increases because the machine (computer) can handle more computations. Every algorithm has some mathematical form, which when implemented in machine code is developed to form a machine learning algorithm. A "training model" is an equation that is formed by applying the data sets to the equation, which is associated with the algorithm. Thus, the RF training model in process block 5300 is created using data sets from process blocks 5000, 5100 and 5200 and applying those data sets to the RF training model, which springs from an RF algorithm.

Since the data sets being analyzed at process block 5300 are relatively large, then the number of possible observations from tree, branch, and leaf-nodes for each tree of the random forest will also be too large to effectively resolve. Thus, the method in FIG. 5 continues with process block 5400, in which the number of features in the data sets are reduced.

At process block 5400, the high order level and number of feature sets is reduced from the feature sets at process block 5300, block 5200, block 5100, and block 5000. In the illustrative embodiment, the Random Intersection Trees (RIT) 5400 training model is used to effectively reduce the high-order levels and number of feature sets from the RF model. RIT reduces the complexity (order) by limiting the observations of features as they traverse the RF to only the features that show main-effect or co-interactivity, i.e., covariate importance.

The method then proceeds to process block 5500 where the covariates from the RIT process block 5400 are ranked. The RIT reduction technique of process block 5400 ranks the most important covariates at process block 5500 by re-interjecting the results back into the RF model (in process block 5300) for further observations.

The method then proceeds to process block 5600 where such observations are then used to form a stump model which further resolves to one or more response surfaces indicating an estimated output pertaining to a specific spatial geometry, which is also referred to as a "voxel." By way of example and not of limitation, the voxel has a specific spatial geometry with defined soil, environmental and yield characteristics. Each voxel then has at least one response surface representing the most important chemical-nutrient or seed-product contributors that generate the model's estimated output response.

Additionally, the stump model response surfaces enable the crop prediction engine 4000 to compute a Reduced Order Surrogate Model (RoSM) represented by the program instructions of process block 5700 to build a Generalized Additive Model (GAM) that further builds a functional equation in the form of a linear function composed of non-linear terms that can be used to easily compute seed and nutrient application recommendations as illustrated by the program instructions of process block 5800 resulting in the form of a downloadable or written prescription file.

The illustrative embodiment of the crop prediction engine 4000 uses a generalized Random Forest (RF) Machine Learning model to understand how input variables (independent variables and covariates) associate and interact with each other through observations of how these input variables traverse decision trees in the random forest. By understanding which input variables as associated with input data sets are coupled to one-another and which are important contributors for crop yield production, users of the system can take actions that explain and recommend where to plant certain seed-types (hybrids and conventional seeds) and what nutrients to apply to achieve the estimated crop predictions.

Thus, the input variables, when applied to the crop prediction model generated with crop prediction engine 4000 can accurately predict an estimated output given a multidimensional set of input features.

The Random Forest (RF) learning model is composed of decision trees. One advantage of decision trees is they may look at data one dimension at a time and use simple rules like less-than, greater-than, yes or no and the like to send operations on a simple binary direction (left or right) for each branch within a single tree. The direction may be based on pre-weighted feature set data where weights may be set for thresholds at each branch resulting in new nodes per branch based on simple binary logic decisions as the tree is built. This process continues recursively from root to branch to leaf until the tree has a fairly homogeneous set of end points called leaf-nodes that can make one simple prediction for the conditional expectation given a single dimensional set, e.g., single feature, of input data.

As an example, a one-dimensional single feature data set may traverse through an RF model. Given a single dimensional decision tree with one dataset "$x_i$," in which (i, i+1, . . . n) where "n" is the total count of numerical input values in "$x_i$" such that all of the splits within the tree are based on one input variable, then each conditional estimated output would resemble a histogram with each leaf node corresponding to one histogram bin. The height of each histogram bin represents the estimated output "$\hat{y}$" for each node in the tree.

In the illustrative embodiment of the crop prediction engine 4000, each additional feature set, which is a data set representing an input feature, of input covariates adds another dimension creating another histogram that changes the conditional estimated output to a higher order function of the input data sets $$\hat{y} = \hat{f}_{RF}(x) = \frac{1}{B}\sum_{b=1}^{B} T_b(x)$$

where: (x) is the multi-dimensional set of input features [$x_i$, $x_j$, $x_k$, . . . $x_p$], p represents the total number of input features, B is the total number of trees in the random forest and $T_b$ represents an ensemble of tree estimators. For each additional input feature additional trees are built to effectively model the higher dimensional predictive output "$\hat{y}$" as a function of the set [$x_i$, $x_j$, $x_k$, . . . $x_p$] of "p" features. In the illustrative embodiment, input features may represent a multiplicity of histograms resulting from a multiplicity of trees that in effect when averaged together generate a smooth function representing the estimated response or predictive output in the higher dimensional space. Thus, in the illustrative embodiment the random forest is used to fit an estimation function that may result in a smooth curve based on a sufficient number of tree estimators used to build the prediction model.

An important differentiator is to observe where the splits are made within the tree. In higher dimensional data, the dimension "p" of input data set matrix [X] is the number of input features and the estimated number of observations in "p" dimensions are estimated to be $\sim 2^p$ resulting in an extremely large number of possible observations to compute and analyze. For example, the soil, environment, and seed variety variables may alone have over 10,000 features or $\sim 2^{10,000}$ observations which may require more computing resources and compute time than economically feasible.

One benefit of using the generalized random forest (RF) model in higher dimensional space is the shallow nature of each tree. In one embodiment, each split (forming a new branch in the tree) in the multi-dimensional forest reduces the number of observations by approximately half since at each split approximately half of the data may be sent to the right of the branch and the other half of the data to the left resulting in an exponential fall-off of feature data from root to final leaf node. This natural reduction in tree depth from the RF model results in the average number of levels of depth to only be approximately $\sim \log_2 N$ where N is the total number of observations represented by the input data sets.

In the illustrative embodiment of the crop prediction engine 4000, the lower number of levels of tree depth for any input data set, represented in input covariates matrix [X] for the possible tree estimators may be exploited to extract the internal data representation from the forest. The exploitation of the data is accomplished by looking for subsets of features that occur together as they transition through the tree from root to leaf. In the observation of the input data as it traverses through the trees the goal is to determine which of the input dependent variables occur together as they traverse the tree from root to leaf. Sets of variables that follow the same path through the tree increases the probability of importance for feature interactions and may contribute or be more important to the estimations made when computing a predictive output. For example, the crop prediction engine takes advantage of the fact that in the simplest form of tree traversal, one observation looks for subsets of variables that pass through the same path from root to leaf. This implies a simple form of a linear equation $\hat{y}=ax_i+\beta x_j+\gamma x_k \ldots$ . Additionally, if $\hat{y}$ represents a function of a complex non-linear equation, the same principle follows when the covariates from different features pass through the same path. The observations assist in determining which subsets of covariates are the most important predictors as computed by the crop prediction engine 4000.

As a result of determining the same path for multiple data sets of inputs, the crop prediction engine 4000 can determine how to map a function for estimated response. In the illustrative embodiment, there is an understanding of the crop responsiveness to a chemical application or an environmental event. When that variance is applied in a specific location it is extremely important information to the agriculture industry. For example, in the simple case of a linear equation of estimated yield, the predictive dependent variable may be written as $\hat{y}=ax_i+\beta x_j+\gamma x_k$ where $\hat{y}$ is the estimated yield output, $x_i$ is one data set which may be organic matter (OM), $x_j$ is another data set which may be the Cation Exchange Capacity CEC, $x_k$ is yet another data set which may be Magnesium (Mg), and where $\alpha$, $\beta$ and $\gamma$ may be specific scaling coefficients for each of the input variable data sets OM, CEC and Mg. In the simple case of a linear equation, one can estimate the predictive change in estimated yield by holding the CEC and Mg input variables constant (assuming beta and gamma are also constants), vary the $\alpha$ coefficient (representing the OM scalar) such that the value of $\alpha$ determines the estimated yield changes for each unit change in OM. The majority of big data modeling seldom follows this simple example. A simple form of a linear equation to estimate yield as the dependent variable is seldom a regular set represented by a linear equation and most likely represents a much higher dimensional response.

Therefore, it is desirable to understand not only the main-effect but also the coupling of different features as one feature may have an effect on another. In the illustrative embodiment of FIG. 5, a novel method is shown that determines which of the subsets have co-dependencies on estimated yield ($\hat{y}$) and what the marginal impact on $\hat{y}$ is as they vary in order to determine chemical nutrients, seed-type applications, and recommendations needed to achieve the desired production output performance.

Based on the well-established binomial theorem, when given a multi-dimensional input set of feature data, the method proceeds to calculate the number of possible observational subsets by $2^p$ where p is the dimensionality of the input data or number of features. In one embodiment, as applied to soil and environmental input characteristics, the number of observational subsets may be beyond the ability to effectively compute the estimated output or to predict the dependent variable output. To reduce the set of observations into something that is manageable, forward regression may be used. The forward regression reduction process follows the law of marginality, which in the illustrative embodiment may not satisfy the accuracy requirements for several reasons.

First, the forward regression training model assumes that the predicted output dependent variable is an additive and multiplicative function. In the field of soil science, the output function may rarely be of this form and is often more complex. Second, an interaction between input characteristics may be important even when the "main-effect" of a single additive term of the function has no or little importance at all.

For example, the forward regression may determine in the estimations that organic matter is not important according to the main-effect of the forward regression training model, but in fact the observation of the interactions of the model for the crop prediction engine may prove it to be one of the most important soil characteristics in the estimation of crop-yield performance. Thus, to reduce the number of observations and keep the accuracy high, for example when observation levels are above order 7 and where use of the forward regression training model falls short of the desired accuracy and quality requirements, the present embodiment uses a novel method to sample into the observational universe of $2^p$ possible observations at substantially reduced computational costs.

In machine learning applications counting of higher order observational subsets based on multi-dimensional sets of input features is difficult and may not be achievable due to the inability to count observations in high dimensional space and having to count first to observe which feature subsets are more frequent in the multi-dimensional feature analysis. For example, given a typical soil and environmental set of input covariates where possible observations may be above order 7 and feature data sets may be above 3,000 the goal of the illustrative embodiment is to determine out of input characteristic features where two or more features occur together and are thus considered to have a high probability of coupling or importance.

The illustrative method implemented by the crop prediction engine 4000 uses the Random Intersection Trees (RIT) training model to reduce the order of observations to just the observations that are considered important to the predictive output response. The illustrative training model utilized by the crop prediction engine 4000 addresses this problem by the use of RIT to compute intersections between binary vectors that represent observations of coupling of covariates as they pass from limb to limb of each tree. For example, RIT is based on the idea that given a product of binary vectors where a "1" in the product vector indicates the position within each binary input vector where there is commonality between two or more observations represented by one or more output binary vectors.

In an alternate embodiment, the RF method of achieving predictive output may be replaced by Neural Networks. In these Neural Networks, the RIT training model may still be applied to reduce high order multi-dimensional data sets, thus reducing the non-responsive observations of the input feature sets.

In the illustrative embodiment, the use of RIT requires that the crop prediction engine 4000 encodes each traversal path through each RF tree from root to leaf into at least one binary vector. For example, for each $[x_i\ x_j,\ x_k,\ \ldots\ x_p]$ input feature on a given path from root to leaf for each tree in the random forest is marked "1" if a particular variable is included and marked "0" if absent in the path through any particular tree. This process may be repeated for all paths in all trees. The resulting binary vectors may be sparse because the terms in a path are typically much shorter than the number of input features in the multi-dimensional data sets represented by $[x_i\ x_j,\ x_k,\ \ldots\ x_p]$. As a first order reduction, once the paths for each tree are encoded into binary vectors a simple bitwise binary product may result in a substantially reduced number of variable sets of observations where the observations are more likely to be coupled and may be more important for the estimated predictions computed by the crop prediction engine 4000. The process as outlined above may be repeated recursively with randomly chosen binary vectors by intersecting them as $Path_n \cap Path_m$ to build random intersection trees. The resulting binary vector is then used to intersect with one or more randomly chosen paths to form the next branch of the RIT. This process may again repeat recursively as additional levels of the RIT are built. The surviving paths at the bottom of the tree that have not been eliminated by calculating the random intersections of other paths (from the process of multiplying binary vector products) will be the paths that are important with strong interactions between coupled covariates from the different input data sets. In the illustrative embodiment, paths represented by "1" at the bottom may be infrequently found as they have survived many binary product intersections based on the number of levels in the RIT. Thus, the output of the RIT may establish the most frequent sets of interactions, hereafter called "item-sets", of which the value for each interaction may be assigned.

Once the solution to the item-set counting problem is solved as outlined above in the illustrative embodiment, and the most frequent solution sets are found, these results may be subsequently used to extract the functions that the RF has previously learned. Based on the illustrative method in FIG. 5, the method has identified and established the multiplicity of dimensional input variables that map together and have a strong non-linear dependence to one another. Additionally, the method of FIG. 5 has established which of the collections of features are also mapped together that also may have a strong non-linear dependence to one another.

The solution of the illustrative method continues by ranking the most frequent observations and sets of observations by the introduction of weighted prevalence. Weighted prevalence may be determined by the product of the measure of node purity and the frequency of the determined item-set found. Node purity of a particular node in any RF tree is determined by a low variance between the coupled variables present at the leaf-node under purity observation. For example, a leaf-node may be considered to be pure if the corresponding voxel has the same yield.

The voxel may represent the geo-spatial location of the smallest cubic area of soil that contains multidimensional soil chemistry and other environmental covariates used for model prediction. The voxel may be a polygonal area representing a two dimensional surface or may be represented by individual points that fall inside the voxels polygonal surface boundary. The points within the voxel may be randomly or non-randomly located and may represent a multidimensional set of input features.

Thus, in the illustrative embodiment the quality of calculation may be ranked by how accurate the predictions are, multiplied by how frequent are the predictions that may result in how important specific features are to the expected response of the output variable. Furthermore, the ranking method as described in the illustrative embodiment puts everything on the same scale. The outcome may be the result of the main-effect or a complex interaction between multiple data set inputs giving interactions in a normalized order between different input item-sets.

Once the quality of the data sets and particular variables within the data sets are ranked for importance, i.e., the main-effect and co-dependencies, the crop prediction engine 4000 uses additional different training models to calculate the optimal response surfaces. Once the important features are resolved then the method applies at least one simple classical regression: plane-fitting by linear regressions, generalized linear modeling, multi-variate regression spline modeling, a lattice network modeling, and the like to build a predictive response surface. Thus, by using the crop prediction engine 4000 to see through the eyes of the random forest and pull the response surface directly out of the random forest, the method of FIG. 5 accurately and quickly predicts the response surface to any variation found in the most important and frequent input variables.

The resulting response surface estimator is called a stump model. The stump model may use a similar method of traversing the RF model as that defined previously but is re-applied with an awareness of ranked importance for both the main-effect and co-dependencies of the input variables. The simplest form of the stump model used for estimated predictions is to use the same one-dimensional method as previously described herein by tracking the splits through the RF model but in a single dimension.

Once the most important coupled covariates are identified, the crop prediction engine 4000 uses at least one computing engine to look at every tree and every path where the coupled covariates occur together, determining the splits for each tree and determining where each split corresponds to a box or stump. This method of stump model usage is similar to the histogram bin as previously described. For example, if the two most significant contributors happen to be CEC and Mg in a single path in a single tree, a simple graph may show the CEC ($x_i$) and Mg ($x_j$) contributions where the height of the stump represents the estimate of yield for the single path in that single tree. The actual total response is the subsequent average of all stumps generated across all significant paths in all trees for the most important contributing variables. The stumps will be of all different shapes, sizes, and values as each is dependent on the paths through the tree estimators used to model the final output prediction. A similar approach may be taken when more than two significant contributors are recognized by the regression through the stump model such that the number of significant contributor variable sets is greater than two.

Thus, the output of stump models results in the derived function for crop yield modeling, resulting in a smoothed surface that represents a non-linear multi-dimensional model for predicting yield. The illustrative embodiment presents at least one method for generating at least one response surface, using the form of a stump model, in the number of dimensions that are important while building a crop prediction engine capable of making accurate crop-yield estimates. The crop-yield response is then based on variances of the important dimensions.

Note, the same method associated with the crop prediction engine may be used for the prediction of other dependent variables such as amounts of carbon sequestration, biofuel generative modeling, life cycle carbon emission models and the like.

The results of the response model, for one or more input dimensions, may be stitched together into the form of a Reduced Order Surrogate Model (RoSM). The RoSM training model can be used to build a Generalized Additive Model (GAM) which represents a linear function of non-linear terms. The resulting GAM may be used as a predictor for any one of the input variables, represented as a high-order curve used for a generalized predictive model for the output prediction of yield as a function of any single important input dimension. In addition to nutrient additives and seed genetics for predictive crop-yields, the GAM response may also be used to predict other dependent output variables such as carbon sequestration, biofuel generative modeling, life cycle carbon emission models and the like.

Once the GAM has been built, making generalized recommendations for crop management and production is streamlined. The RoSM has a dramatically simplified output equation as compared to the complexity of building the predictive model, as understood by the "reduced" order nomenclature in the name Reduced Order Surrogate Model. From the RoSM, the compactness of the model allows for fast and simple predictions. The "Surrogate" component of the nomenclature represents that it is a "Surrogate" of the entire RF model to simplify the productivity of the crop prediction model.

The simplification supports selecting the peaks of the response curves from the predictive RoSM to achieve the application amounts for a predictive crop-yield (output) response. Once the GAM for one or more specific plots of land has been created, it may be used as a standard equation for the crop prediction as a function of the soil, environmental and seed characteristics without needing the entire predictive model apparatus and method.

The normalized yield values and assigned relative maturity values are used as predictor variables for machine learning models. Also, additional hybrid seed properties, crop rotations, tillage, weather observations, soil composition, and other environmental dimensional data sets may also be used as additional predictor variables for the machine learning models.

In the illustrative embodiment, machine learning techniques based on random forests are implemented. In another embodiment neural network modeling may be used instead of RF modeling to determine probability of success scores for hybrid seeds planted at the geo-locations associated with target fields. The dependent variable of the ML model and subsequent modeling is a probabilistic value ranging from 0 to 1, where 0 equals a 0% probability of a successful yield and 1 equals a 100% probability of a successful yield.

In other embodiments, the target variable may be a probabilistic value that may be scaled to fit one or more particular output response types. For example, the dependent output variable for yield may be scaled to bushels per acre with additional scaling for wet or dry measurements. In an embodiment with alternate dependent variable projections, the output may be scaled to represent the return on investment (ROI) based on the delta of hybrid seed costs vs. yield and harvest market prices. A successful yield is described as the likelihood that the yield of a specific hybrid seed is a certain value above the mean yield for similarly classified hybrid seeds. For example, a successful yield may be defined as a yield that is 10 bushels per acre above the mean yield of hybrid seeds that have the same assigned relative maturity value.

In the embodiment where a random forest training model is implemented as the machine learning technique for determining probability of success scores for each of the hybrid seeds for the target fields, the random forest training model may represent an ensemble machine learning method that operates by constructing multiple decision trees during a training period and then outputs the class that is the mean regression of the individual trees. For example, a hybrid seed standup classification may use ML to determine the best seeds based on previous years' yield results. The random forest is used to determine the best seeds based on final yield but also may be used for stand-up output projections based on seed-type, seeding rates, seed depths and other chemical and environmental characteristics. In the method of stand-up projection, the ML model is trained with one or more years of stand-up covariate data from previous years or seasons with hybrid seed, soil, and environmental classifications as additional imported data sets.

The illustrative method of FIG. 5 may also be used to cluster and train the model to predict which hybrids work best for production output based on standup count when target fields have characterized soil and environmental characteristics integrated into the data sets for modeling. Thus, the system and method specified herein may also apply to seed-type varieties such as genetic hybrids. The splits within the trees for every branch would then include moving one direction for one hybrid and/or seed-type and moving in the other direction for a different hybrid and/or seed-type.

In a similar method, the illustrative method of FIG. 5 may also be used to predict crop yield performances of specific hybrid seeds within Geozones defined by local area microclimates. In this embodiment, the model is trained to predict yield based on genetic seed traits and how specific hybrids react to soil chemistry and environmental conditions as a function of different micro-climates. In this example, the model is able to predict the optimum hybrid seed placement to generate the best crop-yield results.

With respect to RF modeling, the process is repeated recursively in the same manner over multiple dimensions of input data sets through all trees in the forest. The process also includes the use of the RIT to reduce the number of observations and further reduction to a linear set of non-linear equations to create a generalized additive model (GAM). Thus, the illustrative embodiment describes how to build an accurate and reliable prediction model for the determination of either optimal stand-up count or optimal yield production based on 1) modeling output from clusters of the soil and environmental characteristics and 2) hybrid and/or seed-type selections within one or more target fields on at least one plot of land.

In one RF embodiment, as described herein to build at least one crop-yield model to predict crop yield, follows the general steps of the method as illustrated in FIG. 5. The first step is to build an RF model as a function of soil chemistry and other available environmental covariates. The second step is to define a distance metric between pairs of feature vectors. The third step is to serve as input to Random Intersection Trees (RIT) that identifies common predictors and interactions within the feature space defined.

The basic approach in the illustrative embodiment for building a crop prediction engine used as a model to estimate as defined in the specification of the illustrative embodiment is based on Random Forest and can be written as an ensemble of tree estimators $T_b(x)$ according to function:

$$\hat{f}_{RF}(x) = \frac{1}{B}\sum_{b=1}^{B} T_b(x)$$

In the function, $\hat{f}_{RF}(x)$, x is a feature vector including: 1) soil chemistry variables such as B, Ca, Cu, Fe, K, Mg, Mn, Na, $NO_3$—N, P, S, Zn, OM, pH, Buffer pH, CEC, and the four percent nutrient saturations % K, % Ca, % Mg, and % Na, from analysis of sparse soil samples and 2) other point-wise environmental features such as soil conductivity, soil texture, elevation or wetness index and the like. And, where B is the total number of trees fitted with b= 1, 2, . . . , B.

Figure 6:
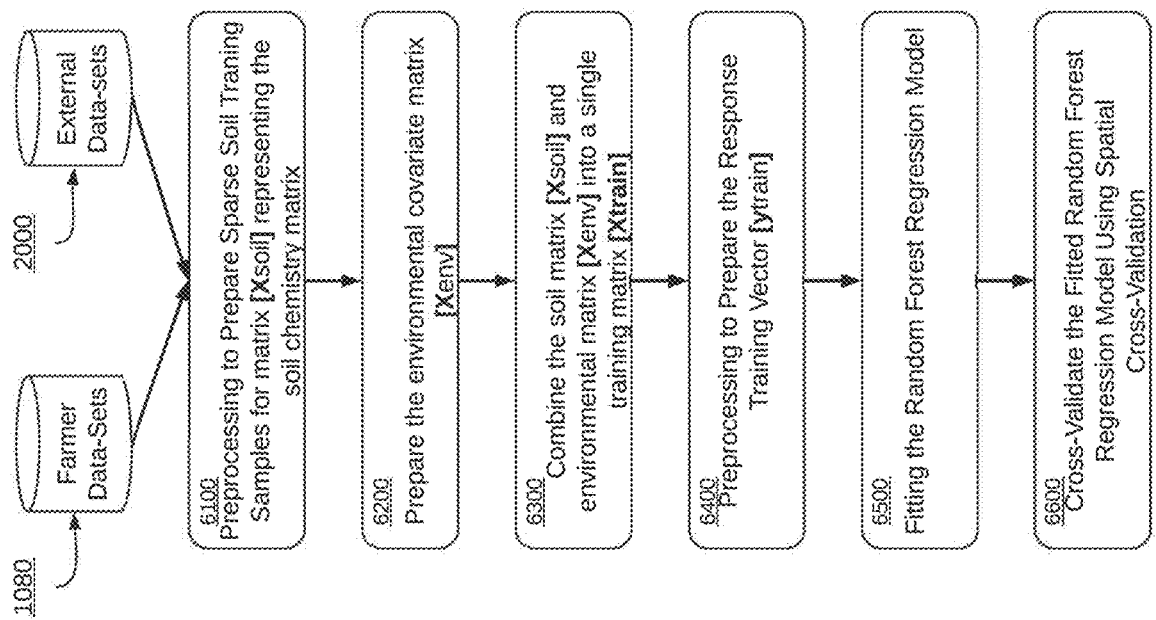
FIG. 6 shows an illustrative flowchart for building and preparing the training vectors used to train a random forest (RF) model.

The process steps of FIG. 6 represent the program instructions for the process steps used to fit the Random Forest yield model according to the illustrative embodiment. Process block 6100 of FIG. 6 represents the program instructions used by the crop prediction engine 4000 in a mathematical representation to prepare one or more sparse soil training matrix $[X_{train}^{soil}]$, as based on the available sparse soil sample analysis of the chemical properties, into subsets as defined herein. Building the multi-dimensional soil input matrix may require a first processing step to make them spatially-independent or sparse from one-another, which enables the sample data sets to achieve independence from possible samples that may be in close proximity of other samples. The spatially-independent covariates are then used to build at least one soil training matrix which is the first step 6100 in preparation to train the crop prediction model 4000. The soil training matrix may be represented mathematically by $X_{train}^{soil}$ ($N \times p^{soil}$), where N is the total number of voxels contained within the bounds of the plot of land being modeled and $p^{soil}$ is the number of soil chemistry variables (soil features) used for modeling the RF observations. Care must be taken in preparing the training observations to ensure that training data are de-noised and spatially-independent. Spatial data encountered in the art of precision agriculture are typically noisy and also may exhibit strong spatial autocorrelation issues. The illustrative embodiment may use Median Smoothing (MS) of one or more of the covariates in the final training matrix $[X_{train}]$ and input response vector $[Y_{train}]$ in the neighborhood of each soil sample to address certain noise issues.

Process block 6200 shows a mathematical representation of the programming instructions used to prepare the environmental training covariate matrix $X_{train}^{env}$. In one embodiment the environmental covariate data may be from one or more data sets such as sampled soil conductivity measurements, elevation values from the neighborhood of $[X_{train}^{soil}]$ or soil texture information from national databases, local weather and moisture measurements, or other localized sensor measurements. Preparation of the said environmental covariates may include one or more processes to de-noise and smooth noisy environmental covariates by one of many illustrative methods such as Median Smoothing applied to each covariate within a neighborhood of each soil sample in data set $[X_{train}^{soil}]$ to form the environmental training matrix. For example, in the illustrative embodiment the spatial geometry in the neighborhood of $[X_{train}^{soil}]$ may be represented by $g_i$ (the geometry of the neighborhood where the environmental variable is located). To de-noise and smooth the environmental training data one embodiment may apply Median Smoothing for each of the environmental covariates at location $g_i$ to form the smoothed environmental covariate training matrix $[X_{train}^{env}](N \times p^{env})$.

Process block 6300 of FIG. 6 represents the program instructions used by the crop prediction engine 4000 in a mathematical representation used to combine the spatially-independent soil covariate training matrix $[X_{train}^{soil}]$ with the de-noised and smoothed environmental covariate training matrix $[X_{train}^{env}]$ into the full training matrix $[X_{train}]$ in the form $X_{train} \equiv [X_{train}^{soil}, X_{train}^{env}]$. The full training matrix is applied to the entire set of voxels in one or more plots of land by applying product matrix $N \times p'$ where $p' = (p^{soil} + p^{env})$ and N represents the total number of voxels within the same one or more plots of land.

Process block 6400 shows a mathematical representation of the programming instructions used to prepare the yield response training vector $y_{train}$. In one embodiment the harvest data from yield monitoring equipment may be densely sampled at a typical sample rate of 1 to 5 Hz. In alternate embodiments the sample rate of the yield monitoring equipment may be different. In one embodiment the yield data set from the yield monitoring equipment at harvest time may be noisy and may contain dense yield data such that pre-processing to de-noise is required and performed by at least one type of Smoothing training model. In the illustrative embodiment Median Smoothing prior to being used as the dependent variable training vector may be performed in the neighborhood of each soil sample in $X_{train}$ to form $y_{train}$, the response training vector. Preparation of a $y_{train}^{noisy}$ response training vector may include one or more processes to de-noise and smooth by one of many illustrative methods such as Median Smoothing the response vector within a neighborhood of each soil sample data set in $[X_{train}^{soil}]$ to form the smoothed response training vector matrix. For example, in the illustrative embodiment the spatial geometry in the neighborhood of $[X_{train}^{soil}]$ may be represented by $g_i$ (the geometry of the neighborhood where the response vector is located). To de-noise and smooth the training response vector one embodiment may apply Median Smoothing to the noisy response vector $y_{train}^{noisy}$ at location $g_i$ to form the smoothed yield training matrix $y_{train}$ ($N \times 1$).

Process block 6500 represents the program instructions used by the crop prediction engine 4000 of the illustrative embodiment, in a mathematical representation used to fit the Random Forest regression model. Fitting may be accomplished by training the RF model with the prepared $X_{train}$ and $y_{train}$ matrices. This procedure 6500 results in a fitted model and may be represented mathematically by:

$$\hat{f}_{RF}(x) = \frac{1}{B}\sum_{b=1}^{B} T_b(x).$$

In the mathematical representation, $\hat{f}_{RF}(x)$ is the fitted model representing the output response from the crop prediction engine with spatial geometry for one or more plots of land as defined by the area of at least one $N \times N$ voxel, (x) represents the combined soil and environmental training vectors ($\vec{x}$ train, $\vec{y}$ train), and $$\frac{1}{B}\sum_{b=1}^{B} T_b$$

represents the Random Forest of B tree estimators.

Figure 7:
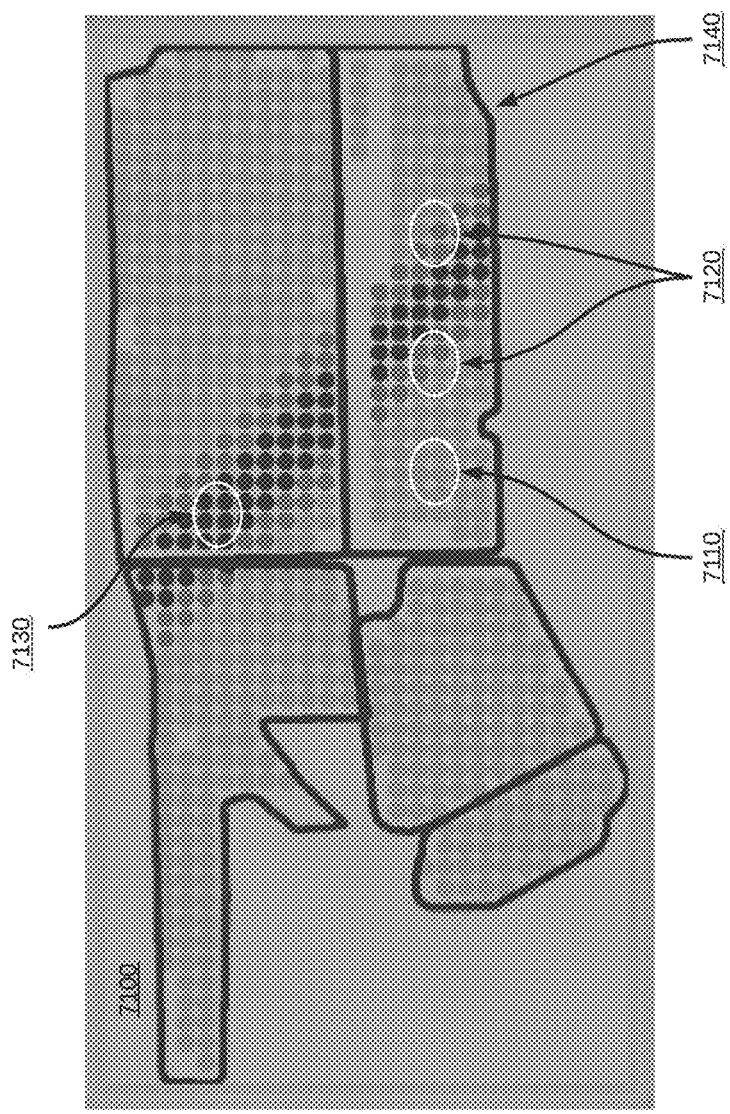
FIG. 7 shows an illustrative spatial image associated with a cross validation framework.

Process block 6600 of FIG. 6 represents the programming instructions used in one embodiment to build a spatial cross-validation framework to facilitate evaluation of the fitted Random Forest. The cross validation may be used to iterate input variable weights and set initial model conditions to reduce $r^2$ error and improve the quality of the crop prediction engine 4000. Cross-Validation (CV) folds can be one or more of: compact circular clusters, horizontal strips, vertical strips, diagonal (south-west to north-east) strips or anti-diagonal (North-west to south-east) strips. FIG. 7 illustrates one example of a set of fields with anti-diagonal cross-validation where the strips represent training data, test data and buffer data. Using the five different spatial CV fold designs helps combat anisotropy in the soil and environmental feature sets that can occur due to the direction in which the field was planted or harvested. The CV method of the illustrative embodiment may permit improved estimates of the model's generalization error. Typically, a buffer of a given size around each CV-fold is set to prevent leakage due to spatial autocorrelation. In one embodiment where data is spatially autocorrected, samples may be present in both the training and test data sets that may force the model's generalization error to be significantly underestimated.

Referring to FIG. 7 there is shown an illustrative spatial image associated with a cross validation (CV) framework. More specifically, FIG. 7 provides an illustrative example of an anti-diagonal cross-validation strip 7100 within the cross-validation framework. Additionally, FIG. 7 shows multiple plots of land with defined geometric polygonal boundaries 7140 used for CV testing. The CV framework in the process block 7100 has a cross-validation strip composed of training data 7110, test data 7120 and buffer data 7130 that is used for validation and tuning of the RF model.

Figure 8:
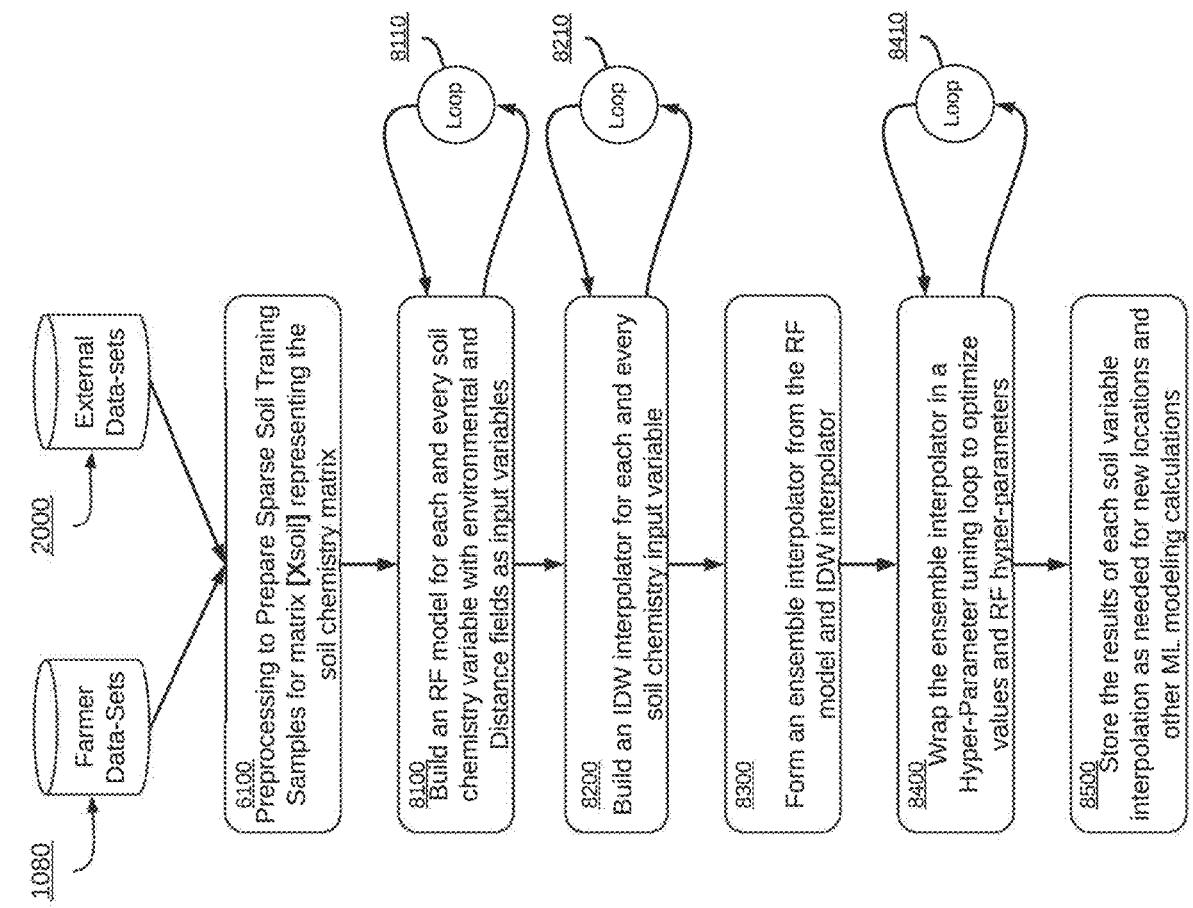
FIG. 8 shows a flowchart of the process for training covariates for estimation of soil characteristics and environmental characteristics at alternate geo-spatial resolutions.

Referring to FIG. 8 there is shown a flowchart of an illustrative process for training covariates for estimation of soil characteristics and environmental characteristics at various geo-spatial resolutions. In the illustrative flowchart of FIG. 8, there are two separate, but complementary, interpolation models that are applied to each soil chemistry variable sampled. The first interpolation model combines a "distance field" with a RF model to generate a Random Forest (RF) interpolation model. The second interpolation model is a specialized model of the Inverse Distance Weighting (IDW) model that is used to estimate the value of each soil chemistry variable at arbitrary locations within one of more plots of land.

In the illustrative embodiment presented in FIG. 8, the ability to estimate soil characteristics and environmental characteristics at different locations within one or more plots of land is used to build training data sets when actual data set from farm sensors is either not available or when sensors are located too sparsely to obtain high spatial-resolution training data for accurate estimations by ML modeling. The illustrative method shown in FIG. 8 can be used for precision accuracy in the delivery of recommendations for additive nutrients and farm management operations. In various embodiments, the method of FIG. 8 may be used for other feature sets and to train the ML models such as yield, weather, elevation, and the like.

In the illustrative embodiment, interpolated soil characteristics, and environmental characteristics, hereafter referred to as "soil chemistry variables" or "soil variables," are used to estimate one or more different clusters of soil variables that are co-dependent or form the main contributors and/or limiters to crop production. In the illustrative embodiment, soil chemistry variables ($\vec{x}$ train) may be defined as having at least one or more of the following illustrative soil chemistry variables: B, Ca, Cu, Fe, K, Mg, Mn, Na, NO3-N, P, S, Zn, OM, pH, buffer pH, CEC, and the four percent nutrient saturations % K, % Ca, % Mg, % Na, and other such soil chemistry variables. In various other embodiments, the soil chemistry variables may include additional soil chemistry variables that are not described.

The method for interpolating soil chemistry variables described provides a high resolution interpolation method, which is generated from the sparse input training data. Additionally, a clustering analysis and ranking the co-dependent soil variables is performed, which allows the ML models to provide recommendations for managing the soil chemistry variables. By way of example and not of limitation, the recommendations may identify the need to add, reduce or balance one or more soil variable quantities to optimize yield production efficiency and improve soil health. Thus, the system and method for interpolating soil chemistry variables permits the estimation of soil chemistry variables at any location within one or more plots of land at any location with a limited data set of soil chemistry variables.

At process block 8100, the first interpolation model combines a "distance field" with a RF model to generate a Random Forest (RF) interpolation model. In the illustrative embodiment, the RF interpolation model looks at each soil chemistry variable to build a forest of tree estimators fitted with at least one set of "ancillary covariates" such as soil chemistry, soil conductivity or other environmental covariates. Other ancillary covariates include, but are not limited to, growing days, planting dates, moisture indexing, local weather conditions such as rain accumulation, wind, temperature, humidity, average sunlight based on cloud cover or sunlight hours, Soil organic matter, texture, top-soil depth, fertility indexes, and soil electro conductivity.

In general, "distance fields," which are also known as a "distance map" or a "distance transform" are used to generate spatial predictors, which are then supplied to the RF model. For the purposes of this patent, the term "distance fields" is defined as a representation of the distance from any point or variable value to the closest point or variable value within a domain of points or variable values in one or more data-sets. The domain may represent a set of similar dependent or independent variables consisting of geospatial, chemical, environmental, or other variable types.

The illustrative embodiment uses a Euclidean Distance Field (EDF) to supply the random forest (RF) model with several spatial predictors. The fitted RF model is denoted as $\hat{f}_{RF}(a)$, where a are the ancillary variables. The fitted RF model is then used to predict the values of the dependent variables at arbitrary locations within one or more plots of land.

In alternative embodiments, other interpolation models such as ordinary kriging (OK), regression kriging (RK), geographically weighted regression (GWR), contextual spatial modeling (CSM), and the like may be used as various spatial predictors for EDF. In yet another alternative embodiment, bagged multivariate adaptive regression splines (MARS), support vector machines (SVM), Cubist, Neural Network (NN) and the like may be used as machine learning alternatives to the machine learning RF method of the illustrative embodiment.

At process block 8200, the second interpolation model is a specialized model of the Inverse Distance Weighting (IDW) model that is used to estimate the value of each soil chemistry variable at arbitrary locations within one or more plots of land. The IDW interpolation method is used to obtain a smart smoothing effect based on the assumption that in the field of geography everything is related to everything else, but near things are more related than distant things. The assumption ensures that soil samples closer to a point of interpolation are weighted more heavily than soil samples that are more distant, as known to those skilled in the art and shown by the mathematical representation:

$$\hat{f}_{IDW}(s) = z(s) = \begin{cases} \dfrac{\sum_i \omega_i(s) z_i}{\sum_i \omega_i(s)}, & \text{if } s \neq s_i \text{ for all } i, \\ z_i, & \text{if } s = s_i \text{ for some } i, \end{cases}$$

where:

$$\omega_i(s) = \begin{cases} \dfrac{1}{\|s - s_i\|^p}, & \text{if } \|s - s_i\| < r, \\ 0, & \text{otherwise}, \end{cases}$$

and:

$$\{(s_1, z_1), (s_2, z_2), \ldots (s_N, z_N),\}$$

represents the set of N known locations ($\vec{s}_i$), and values ($\vec{z}_i$) for each soil chemistry variable, and where r and p are search radius and power parameters, respectively. The weighting coefficient $\omega_i(s)$ decreases as the distance increases from the interpolated point such that the resulting geo-spatial regions defined by radius r surrounding the interpolated points $\hat{f}_{IDW}(s)$ resolves into a set of mosaic tiles, hereinafter referred to as the "IDW-voxels" or "voxels" that are used to define an area of a plot of land representing a smoothed nearly constant multivariate surface for larger values of power variable p and within the area of the radius r.

In the illustrative embodiment, where the soil chemistry variables approach M dimensions, and soil sample locations ($\vec{s}_i$) are far away the power p is set closer to the value of the total number of dimensions M and the radius r is increased to encompass a larger interpolation area. Thus, for computation using the IDW interpolation method, the dynamic parameterizations of r and p may be varied and optimized based on the calculation of the density estimation of points within the area of circumference of distances $r_0$ (center) to R (circumference). Other forms of distance weighting may also be used such as Lukaszuk-Karmowski metric or modified Shepard's method.

FIG. 8 presents a flowchart that includes feature-set storage and programing instruction flow, which is used to estimate soil variables at any location within one or more plots of land. As previously described, feature set data is collected and stored as either farmer data-sets 1080 (typically from sensors local to one or more plots of land) or from remote sensors, government agencies, agricultural groups and the like stored as external or third party data-sets 2000. The stored data of the illustrative embodiment undergoes several stages of data pre-processing in preparation for ML model training. In the illustrative embodiment, pre-processed soil variables along with their known sampling locations are used to build at least one soil training matrix [$X_{soil}$] as shown in process block 6100, which is associated with FIG. 6.

The soil training data at block 8100 is used to build an interpolated data set at loop 8110 of random forest models that are used to estimate at least one soil variable using at least one environmental and at least one distance field vector to train the multiplicity of RF tree estimators used for each soil variable. The estimated RF interpolation outputs are the dependent output variables of the RF models, in which each output includes a single feature variable from the multi-dimensional soil variable matrix. In operation, the RF interpolation models may be run multiple times at loop 8110, typically in a program loop, for each independent soil variable that is to undergo interpolation.

Continuing to process block 8200, the method implements a second interpolation model. By way of example and not of limitation, the second interpolation model includes an Inverse Distance Weighting (IDW) model for each soil chemistry variable. In the illustrative embodiment, the IDW interpolation model may run at loop 8210, which calculates each soil chemistry variable ($z_i$) at N known locations that are represented by one or more location vectors ($s_i$). Note, for each soil chemistry variable having IDW parameters r (radius) and p (power), the IDW parameters are used to define the interpolation bounds and smoothing factors, respectively.

At process block 8300, the method continues by forming an ensemble of the RF and IDW interpolation models for each soil chemistry output variable that is "blended." The combined "complementary interpolator" at block 8300 may be represented as a form of the RF+IDW ensemble interpolator represented by:

$$\hat{f}_{RF+IDW}{}^v(a,s)$$

where v is one of the soil chemistry variables to be interpolated from the [$X_{soil}$] input covariate matrix and $\vec{a}$ represents the vector of ancillary input variables from the RF interpolator model, which is used to predict the values of the variable at arbitrary locations within one or more plots of land. Additionally, v represents the individual soil chemistry variable under interpolation and $\vec{s}$ represents the IDW point geometry location vector for the IDW input covariates $y_{train}{}^v$ and $x_{train}{}^{env}$ to be used.

The ensemble of the RF and IDW models 8300 is then used to calculate a non-optimized interpolated soil chemistry variable v as a function of the blending term $\alpha$, which may be represented by the ensemble blending equation;

$$\hat{f}_{RF+IDW}{}^v(a,s) = \alpha \hat{f}_{RF}(a) + (1-\alpha) \hat{f}_{IDW}(s)$$

By using a linear combination of these two complementary interpolation models, the combination of the strengths of both methods such that the random forest model compromises smoothness of the solution for accuracy, while the IDW model does the opposite by compromising accuracy for smoothness.

The method then proceeds to process block 8400 where a hyper-parameter tuning loop 8410 is used for optimization of the blending term $\alpha$ and the IDW model parameters r (radius) and p (power) used to optimize each interpolated soil chemistry variable from the entire feature set of soil chemistry variables. Discontinuities and spatial variations of soil characteristics found in different plots of land are resolved by constructing error surfaces and adaptively partitioning the interpolated surfaces.

The hyper-parameter tuning loop 8410 uses the multi-fold cross validation method for parameter tuning as illustrated in FIG. 7. To assess the interpolation accuracy, error terms are calculated for each fold of the multifold cross validation surface. In the illustrative embodiment, a ten-fold cross validation method is implemented by splitting the data samples for each soil chemistry into folded cross validation strips using a portion of the input samples for interpolation and a portion for the multi-fold cross validation.

In one embodiment the error terms may be calculated by comparing different methods of error calculation and using at least one of the following methods: mean error (ME), mean absolute error (MAE), mean relative error (MRE), root mean square error (RMSE) and other such methods of error calculation. In the illustrative embodiment, the coefficient of determination or $R^2$ (R squared) error provides a measure of how well observed outcomes are replicated by the model. The $R^2$ error may be used to effectively normalize the error term where the accuracy is sufficient for hyper-parameterization optimizations.

More generally, hyper-parameter optimization at block 8400 uses programmatic loops 8410 with a fixed set of estimated α, r and p parameters for loop initialization for at least each soil variable and each fold in the CV framework as illustrated in part by FIG. 7. Samples from the input feature sets of training data are composed of training data 7110, test data 7120, and buffer data 7130 for tuning.

The error terms are calculated and compared to at least one tuning loop with each of the tuning parameters adjusted for least error in each hyper-tuning-loop of the RF+IDW ensemble interpolator. In various embodiments, where the discontinuities and spatial variations of soil characteristics are relatively homogeneous across one or more plots of land, the hyper-parameter tuning loop may not be needed or used to obtain reasonable adaptive partitioning of the interpolated soil variable surfaces. In an alternative embodiment, the number of soil chemistry variables to be interpolated may be reduced by a first pass calculation by the crop prediction engine 4000. The first pass response may determine the important soil variables that contribute a main-event or, within a group of coupled soil chemistry variables the important contributors to one or more crop-yield or seed-type yield response surfaces. Thus, the set of soil chemistry variables applied to the soil interpolation method may be reduced in number by first observations from ML modeling of the important soil chemistry variables in one or more plots of land.

The method then continues to process block 8500 and stores the resulting optimized interpolated soil chemistry values ($z_i$) for each of the estimated locations ($s_i$) into one or more storage devices, which are connected to the application computing cluster 4100 application database 4150 or the data science computing cluster 4300 data set database 4350 or in disk storage 4030 for use by the crop prediction engine 4000.

It is to be understood that the detailed description of illustrative embodiments is provided for illustrative purposes. Thus, the degree of software modularity for the transactional system and method presented above may evolve to benefit from the improved performance and lower cost of the future hardware components that meet the system and method requirements presented. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A method for interpolating soil chemistry variables to a plurality of plots of land, the method comprising:
   providing a geospatial database associated with a crop prediction engine, wherein the geospatial database receives a plurality of soil composition information for each of the plurality of plots of land;
   accessing the plurality of soil composition information for each of the plurality of plots of land, in which the soil composition information includes at least one of a plurality of measured soil sample results, a plurality of environmental results, and a plurality of soil conductivity results;
   applying, by the crop prediction engine, a first interpolation training model and a second interpolation training model, wherein the first interpolation training model includes a machine learning training model and a distance field training model, wherein the second interpolation training model includes a distance weighting training model;
   receiving, by the machine learning training model, the plurality of soil composition information;
   generating, by the distance field training model, a plurality of spatial predictors;
   applying the plurality of spatial predictors to the machine learning training model;
   prioritizing, by the first interpolation training model, spatial smoothing over accuracy, in which spatial smoothing removes inaccurate interpolated results and accuracy relates to the degree the interpolated results conform to a correct value;
   weighing more greatly, by the distance weighting training model, interpolated soil composition information closer to a point of interpolation than interpolated soil composition information that is further away to the point of interpolation;
   prioritizing, by the second interpolation training model, accuracy over spatial smoothing;
   estimating, at the crop prediction engine, a plurality of soil chemistry values at a plurality of different locations with the first interpolation training model and the second interpolation training model;
   performing, by the crop prediction engine, first pass calculations using measured samples;
   determining, by the crop prediction engine, from the first pass calculations one or more soil variables of a plurality of soil variables included in the soil composition information that are important soil chemistry contributors to at least one of a crop-yield response surface and a seed-type response surface; and
   reducing, by the crop prediction engine, the soil composition information received by the first interpolation training model and the second interpolation training model to the one or more soil variables that are important soil chemistry contributors to at least one of the crop-yield response surface and the seed-type response surface.

2. The method of claim 1 further comprising generating, at the crop prediction engine, a plurality of non-optimized interpolated soil chemistry values by blending the first interpolation training model and the second interpolation training model with a blending term that separately weighs the first interpolation training model and the second interpolation training model.

3. The method of claim 1 further comprising optimizing, at the crop prediction engine, the blending of the first interpolation training model and the second interpolation training model by performing one or more error calculations.

4. The method of claim 2 further comprising optimizing, at the crop prediction engine, the blending of the first interpolation training model and the second interpolation training model by performing one or more error calculations.

5. The method of claim 4 wherein the optimizing, at the crop prediction engine, the blending of the first interpolation training model and the second interpolation training model includes applying a hyper parameter tuning loop to the first interpolation training model and the second interpolation training model,
   wherein the hyper parameter tuning loop optimizes blending the first interpolation training model and the second interpolation training model by performing one or more error calculations.

6. The method of claim 5 wherein the machine learning model associated with the first interpolation training model includes a random forest prediction model.

7. The method of claim 6 wherein the distance weighting training model includes inverse distance weighting (IDW).

8. A system for interpolating soil chemistry variables to a plurality of plots of land, the system comprising:
   a geospatial database associated with a crop prediction engine, wherein the geospatial database receives a plurality of soil composition information for each of the plurality of plots of land, in which the soil composition information includes at least one of a plurality of measured soil sample results, a plurality of environmental results, and a plurality of soil conductivity results;
   the crop prediction engine applies a first interpolation training model that includes a machine learning model, which receives the plurality of soil composition information, and a distance field training model that generates a plurality of spatial predictors that are applied to the machine learning model, wherein the first interpolation training model prioritizes spatial smoothing over accuracy, in which spatial smoothing removes inaccurate interpolated results and accuracy relates to the degree the interpolated results conform to a correct value;
   the crop prediction engine applies a second interpolation training model that includes a distance weighting training model that more greatly weighs interpolated soil composition information closer to a point of interpolation than interpolated soil composition information that is further away to the point of interpolation, wherein the second interpolation training model prioritizes accuracy over spatial smoothing;
   the crop prediction engine estimates a plurality of soil chemistry values at a plurality of different locations with the first interpolation training model and the second interpolation training model;
   wherein the crop prediction engine performs first pass calculations using measured soil samples to determine one or more soil variables of a plurality of soil variables included in the soil composition information that are important soil chemistry contributors to at least one of a crop-yield response surface and a seed-type response surface; and
   wherein the crop prediction engine reduces the soil composition information received by the first interpolation training model and the second interpolation training model to the one or more soil variables that are important soil chemistry contributors to at least one of the crop-yield response surface and the seed-type response surface.

9. The system of claim 8 wherein the crop prediction engine generates a plurality of non-optimized interpolated soil chemistry values by blending the first interpolation training model and the second interpolation training model with a blending term that separately weighs the first interpolation training model and the second interpolation training model.

10. The system of claim 8 wherein the crop prediction engine optimizes the blending of the first interpolation training model and the second interpolation training model by performing one or more error calculations.

11. The system of claim 9 wherein the crop prediction engine optimizes the blending of the first interpolation training model and the second interpolation training model by performing one or more error calculations.

12. The system of claim 11 wherein the crop prediction engine optimization of the blending of the first interpolation training model and the second interpolation training model includes applying a hyper parameter tuning loop to the first interpolation training model and the second interpolation training model,
   wherein the hyper parameter tuning loop optimizes blending the first interpolation training model and the second interpolation training model by performing one or more error calculations.

13. The system of claim 12 wherein the machine learning model associated with the first interpolation training model includes a random forest prediction model.

14. The system of claim 13 wherein the distance weighting training model includes inverse distance weighting (IDW).

15. A method for interpolating soil chemistry variables to a plurality of plots of land, the method comprising:
   accessing a plurality of soil composition information for each of the plurality of plots of land, in which the soil composition information includes at least one of a plurality of measured soil sample results, a plurality of environmental results, and a plurality of soil conductivity results;
   applying, by the crop prediction engine, a first interpolation training model and a second interpolation training model, wherein the first interpolation training model includes a machine learning training model and a distance field training model, wherein the second interpolation training model includes a distance weighting training model;
   receiving, by the machine learning training model, the plurality of soil composition information;
   generating, by the distance field training model, a plurality of spatial predictors;
   applying the plurality of spatial predictors to the machine learning training model;
   prioritizing, by the first interpolation training model, spatial smoothing over accuracy, in which spatial smoothing removes inaccurate interpolated results and accuracy relates to the degree the interpolated results conform to a correct value;
   weighing more greatly, by the distance weighting training model, interpolated soil composition information closer to a point of interpolation than interpolated soil composition information that is further away to the point of interpolation;
   prioritizing, by the second interpolation training model, accuracy over spatial smoothing;

estimating a plurality of soil chemistry values at a plurality of different locations with the first interpolation training model and the second interpolation training model;

performing first pass calculations using measured soil samples;

determining from the first pass calculations one or more soil variables of a plurality of soil variables included in the soil composition information that are important soil chemistry contributors to at least one of a crop-yield response surface and a seed-type response surface; and reducing the soil composition information received by the first interpolation training model and the second interpolation training model to the one or more soil variables that are important soil chemistry contributors to at least one of the crop-yield response surface and the seed-type response surface.

16. The method of claim 15 further comprising generating a plurality of non-optimized interpolated soil chemistry values by blending the first interpolation training model and the second interpolation training model with a blending term that separately weighs the first interpolation training model and the second interpolation training model.

17. The method of claim 15 further comprising optimizing the blending of the first interpolation training model and the second interpolation training model by performing one or more error calculations.

18. The method of claim 15 wherein the optimizing the blending of the first interpolation training model and the second interpolation training model includes applying a hyper parameter tuning loop to the first interpolation training model and the second interpolation training model, wherein the hyper parameter tuning loop optimizes blending the first interpolation training model and the second interpolation training model by performing one or more error calculations.

19. The method of claim 15 wherein the machine learning model associated with the first interpolation training model includes a random forest prediction model.

20. The method of claim 15 wherein the distance weighting training model includes inverse distance weighting (IDW).

* * * * *